(12) United States Patent
Mallard et al.

(10) Patent No.: US 10,772,807 B2
(45) Date of Patent: Sep. 15, 2020

(54) LIPID MICROCAPSULES PREFERABLY COMPRISING A RETINOID, AND COMPOSITION CONTAINING SAME, METHOD FOR THE PRODUCTION THEREOF, AND USE OF SAME IN DERMATOLOGY

(71) Applicant: GALDERMA RESEARCH & DEVELOPMENT, Biot (FR)

(72) Inventors: Claire Mallard, Mougins (FR); Carole Dubayle, Mouans-Sartoux (FR)

(73) Assignee: GALDERMA RESEARCH & DEVELOPMENT, Biot (FR)

( * ) Notice: Subject to any disclaimer, the term of this patent is extended or adjusted under 35 U.S.C. 154(b) by 0 days.

(21) Appl. No.: 15/101,721

(22) PCT Filed: Dec. 4, 2014

(86) PCT No.: PCT/EP2014/076658
§ 371 (c)(1),
(2) Date: Jun. 3, 2016

(87) PCT Pub. No.: WO2015/082659
PCT Pub. Date: Jun. 11, 2015

(65) Prior Publication Data
US 2016/0310439 A1    Oct. 27, 2016

(30) Foreign Application Priority Data

Dec. 4, 2013  (FR) ........................ 13 62117

(51) Int. Cl.
| | | |
|---|---|---|
| *A61K 8/11* | (2006.01) | |
| *A61K 9/00* | (2006.01) | |
| *A61K 9/06* | (2006.01) | |
| *A61K 31/402* | (2006.01) | |
| *A61Q 19/00* | (2006.01) | |
| *A61K 31/192* | (2006.01) | |
| *A61K 8/37* | (2006.01) | |
| *A61K 31/203* | (2006.01) | |
| *A61K 8/67* | (2006.01) | |
| *A61K 8/86* | (2006.01) | |
| *A61K 31/216* | (2006.01) | |
| *A61K 9/50* | (2006.01) | |
| *A61K 8/55* | (2006.01) | |
| *A61K 9/107* | (2006.01) | |
| *A61K 31/05* | (2006.01) | |
| *A61K 31/12* | (2006.01) | |
| *A61K 31/5575* | (2006.01) | |
| *A61K 31/573* | (2006.01) | |
| *A61K 9/08* | (2006.01) | |
| *A61K 47/10* | (2017.01) | |
| *A61K 47/14* | (2017.01) | |
| *A61K 47/24* | (2006.01) | |

(52) U.S. Cl.
CPC .............. *A61K 8/11* (2013.01); *A61K 8/37* (2013.01); *A61K 8/375* (2013.01); *A61K 8/553* (2013.01); *A61K 8/671* (2013.01); *A61K 8/86* (2013.01); *A61K 9/0014* (2013.01); *A61K 9/06* (2013.01); *A61K 9/08* (2013.01); *A61K 9/107* (2013.01); *A61K 9/5015* (2013.01); *A61K 31/05* (2013.01); *A61K 31/12* (2013.01); *A61K 31/192* (2013.01); *A61K 31/203* (2013.01); *A61K 31/216* (2013.01); *A61K 31/402* (2013.01); *A61K 31/5575* (2013.01); *A61K 31/573* (2013.01); *A61K 47/10* (2013.01); *A61K 47/14* (2013.01); *A61K 47/24* (2013.01); *A61Q 19/00* (2013.01); *A61K 2800/412* (2013.01)

(58) Field of Classification Search
None
See application file for complete search history.

(56) References Cited

U.S. PATENT DOCUMENTS

| | | | | |
|---|---|---|---|---|
| 5,100,591 A | * | 3/1992 | Leclef .................. | A61K 9/1617 264/4.1 |
| 5,227,165 A | | 7/1993 | Domb et al. | |
| 6,017,549 A | * | 1/2000 | Knight ..................... | A61K 8/06 424/401 |
| 7,781,489 B2 | | 8/2010 | Menegatti et al. | |
| 7,807,708 B2 | * | 10/2010 | Biadatti ................ | C07C 229/52 514/428 |
| 8,057,823 B2 | | 11/2011 | Heurtault et al. | |
| 8,110,284 B2 | | 2/2012 | Naigertsik et al. | |

(Continued)

FOREIGN PATENT DOCUMENTS

| | | |
|---|---|---|
| FR | 2805761 A1 | 9/2001 |
| WO | 91/07171 A1 | 5/1991 |

(Continued)

OTHER PUBLICATIONS

English Translation of the International Search Report dated Jan. 9, 2015 corresponding to International Patent Application No. PCT/EP2014/076658, 4 pages.

(Continued)

*Primary Examiner* — Melissa L Fisher
(74) *Attorney, Agent, or Firm* — Foley & Lardner LLP; S. Talapatra

(57) ABSTRACT

Lipid microcapsules are described that can include at least one irritant active substance, more specifically a retinoid, in a soluble form. Also described, are pharmaceutical compositions comprising the same, and methods for the production thereof. A method of using the composition to treat dermatological pathologies is also described.

32 Claims, 4 Drawing Sheets

(56) References Cited

U.S. PATENT DOCUMENTS

| | | |
|---|---|---|
| 8,309,121 B2 | 11/2012 | Baudonnet et al. |
| 2005/0048088 A1 | 3/2005 | Zulli et al. |
| 2007/0134276 A1 | 6/2007 | Menegatti et al. |
| 2007/0184076 A1 | 8/2007 | Unger et al. |
| 2008/0167375 A1 | 7/2008 | Weidner |
| 2008/0193393 A1 | 8/2008 | Dayan |
| 2009/0258065 A1* | 10/2009 | Baudonnet ........... A61K 9/0014 424/452 |
| 2010/0098752 A1 | 4/2010 | Pinsky |
| 2011/0195030 A1 | 8/2011 | Mumper et al. |
| 2015/0125520 A1 | 5/2015 | Mallard |
| 2016/0310439 A1 | 10/2016 | Mallard et al. |

FOREIGN PATENT DOCUMENTS

| | | |
|---|---|---|
| WO | WO-95/03829 A1 | 2/1995 |
| WO | 2006/066978 A1 | 6/2006 |
| WO | WO-2010/063774 A1 | 6/2010 |
| WO | WO-2010/072958 A2 | 7/2010 |
| WO | 2010/113111 A1 | 10/2010 |
| WO | 2011/036234 A1 | 3/2011 |
| WO | 2013/178749 A1 | 12/2013 |

OTHER PUBLICATIONS

International Search Report dated Jan. 9, 2015 corresponding to International Patent Application No. PCT/EP2014/076658, 5 pages.
Written Opinion of the International Searching Authority dated Jan. 9, 2015 corresponding to International Patent Application No. PCT/EP2014/076658, 7 pages.
International Search Report and Written Opinion issued in International Patent Application No. PCT/EP2013/061189, dated Aug. 9, 2013.

* cited by examiner

LIPID MICROCAPSULES PREFERABLY COMPRISING A RETINOID, AND COMPOSITION CONTAINING SAME, METHOD FOR THE PRODUCTION THEREOF, AND USE OF SAME IN DERMATOLOGY

CROSS-REFERENCE TO PRIOR APPLICATIONS

This application is a National Stage of PCT/EP2014/076658, filed Dec. 4, 2014, and designating the U.S. (published on Jun. 11, 2015, as WO 2015/082659 A1), which claims priority under 35 U.S.C. § 119 to French Patent Application No. 1362117, filed Dec. 4, 2013, each hereby expressly incorporated by reference in its entirety and each assigned to the assignee hereof.

The present invention relates to lipid microcapsules which have an oily internal phase and a non-polymeric shell obtained from at least one lipid compound chosen from amphiphilic lipids.

In particular, the invention relates to microcapsules comprising an irritant active ingredient and more particularly a retinoid compound, said irritant active ingredient being present in dissolved form in the microcapsules comprising an oily core.

The invention also relates to the primary emulsion composed of the microcapsules comprising an oily core, dispersed in an aqueous phase, and to the pharmaceutical composition comprising the primary emulsion in a pharmaceutically acceptable carrier.

The invention also relates to the process for preparing the primary emulsion, and the pharmaceutical composition comprising the lipid microcapsules. Finally, the invention relates to a composition for use thereof in the treatment of dermatological complaints, in particular acne.

Those skilled in the art know that the activity of certain pharmaceutical active ingredients is inseparable from a certain level of irritation. It is, however, essential to find compositions for maintaining the biological activity of the active ingredient while at the same time minimizing its irritant nature. Retinoids are active agents commonly used in dermatology, but the majority are known as being irritant active ingredients. It is therefore important, while maintaining the pharmaceutical activity, to improve the tolerance of this family of antiacne molecules.

The prior art discloses several formulation patents for improving the topical tolerance of irritant active ingredients, in particular in the case of retinoids, by adding anti-irritant compounds to the composition.

The Applicant has protected in patent FR 2 894 820 galenical formulations using anti-irritants such as allantoin or EDTA in combination with a particular retinoid, adapalene.

In patent application WO 2006/037552, the inventors add constituents to the formulation base such as interleukin-8 inhibitor to act on the irritation process.

In patent application WO 2005/079775, the inventors improve the tolerance of retinoids by adding idebenone or a derivative thereof.

Won et al., U.S. Pat. No. 5,955,109, incorporate a retinoid into porous microspheres (Microsponge®) to reduce the release of the retinoid into the layers of the skin, which gives rise to a decrease in the level of irritation by controlling the release kinetics of the active agent through the skin.

In patent application WO 2005/039532, the authors use a retinoid in an oil-in-water microemulsion for the purpose of improving the bioavailability. This microemulsion is composed of a phospholipid and of a sodium hyaluronate or modified hyaluronic acid.

Saurat et al. in patent FR 2 865 651 propose the combination of a retinoid with one or more hyaluronate fragments in a formulation for dermatological use in the case of treatments for which it will be necessary to improve the condition of the skin.

Cattaneo in patent US 2005/0281886 discloses chitosan microparticles and nanoparticles containing a retinoid. These microparticles and nanoparticles generated by a high-viscosity chitosan reduce the irritant effect of the retinoids.

There are in the prior art many encapsulation techniques which make it possible to obtain microcapsules.

The term "microencapsulation" defines all of the technologies which make it possible to obtain the preparation of individualized microparticles, consisting of a coating material containing an active material.

The terminology "microcapsules" implies entities of which the diameter is between 1 and 1000 μm. The term "nanocapsules" is reserved for capsules of which the size is less than 1 micron.

The substance encapsulated may be in the form of fine particles of divided solid, of a liquid, or of a gaseous compound. The microcapsule makes it possible to preserve the encapsulated substance in the form of a finely divided state, and to release it under the desired conditions.

The microparticles obtained by microencapsulation may be in two types of distinct morphologies:
  microspheres which are particles consisting of a continuous macromolecular or lipid network forming a matrix in which the active material is finely dispersed. The latter may be in the form of solid fine particles or else of droplets of solution;
  microcapsules which are reservoir particles consisting of a core of liquid or solid active material, surrounded by a continuous solid shell of coating material.

The various microencapsulation methods can be categorized according to various criteria. Richard and Benoit, (Microencapsulation, 2000, Techniques de l'Ingénieur [Techniques of the Engineer], J2210, 1-20) propose four different ways to categorize encapsulation methods:
  the processes can be categorized according to whether or not organic solvent is used, some techniques, such as complex coacervation, using supercritical fluids,
  the nature of the dispersing medium can also be used as a basis for a categorization: it may be liquid (interfacial polycondensation, coacervation), gaseous (spray drying, fluidized bed coating), or in the supercritical state (phase separation),
  the family to which the compound used to obtain the capsule belongs may also make it possible to categorize the encapsulation modes: it is possible to use preformed polymers (coacervation), lipids (spray-congealing), or else monomers (interfacial polycondensation, polymerization in a dispersed medium),
  finally, a last categorization is based on the nature of the ingredient according to which the microencapsulation is carried out:
  physicochemical processes are distinguished from chemical and mechanical processes.

The various encapsulation methods are summarized in the table presented below according to the nature of the process (Finch and Bodmeier, 2005, Microencapsulation, Wiley-VCH verlag GmbH & Co, KGa, Weinheim10.1002/14356007.a16_575).

| Type of process | Encapsulation mode | Microparticle size range | Type of products obtained |
|---|---|---|---|
| Physicochemical processes | Phase separation or coacervation (simple or complex) | 2-1200 μm | Microcapsules |
| | Evaporation-solvent extraction | 0.5-200 μm | Microcapsules Microspheres |
| | Melting of the encapsulation material (hot melt) | | Microspheres |
| | Thermal gelling of emulsion | | Microspheres |
| Chemical processes | Interfacial polycondensation/ polymerization | 2-2000 μm | Microcapsules Microspheres |
| | Radical or anionic polymerization in a dispersed medium | | Microspheres |
| Mechanical processes | Spray drying/atomization | 1-200 μm | Microspheres |
| | Gelling or freezing of drops (prilling) | 200-800 μm | Microspheres |
| | Fluidized air bed coating (spray-coating) | 35-5000 μm | Microspheres |
| | Extrusion/spheronization | 200 μm | Microspheres |

Since the mechanical processes make it possible to obtain only microspheres, microcapsules are generally obtained by means of physicochemical or chemical processes. These processes require the use of preformed coating agents such as polymers or monomers which, in situ via a specific polymerization mechanism, allow the formation of the coating material.

Figure 1:
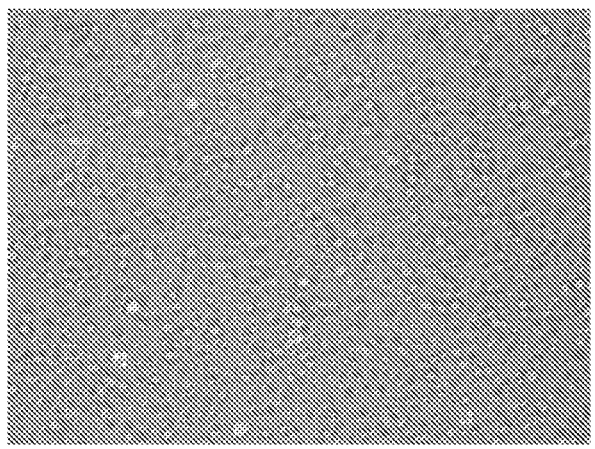
FIG. 1 is a photo image under microscope (objective 40 and magnification x252) of the microcapsules in gel No. 1 prepared from the primary emulsion D containing PPG-15 Stearyl ether as oil, according to the examples.

In accordance with the present invention as defined hereinafter, the microcapsules and processes which make it possible to obtain them have the advantage, compared with the prior art, of not containing any polymer or any volatile organic solvent and of not involving temperature cycles.

According to the invention, the term "volatile solvent" is intended to mean any solvent considered to be unstable, i.e. having a boiling point strictly below 100° C. By analogy, any solvent having a boiling point above or equal to 100° C. will be considered nonvolatile according to the invention.

In the case of the majority of applications of microencapsulation, the active substances are firstly held and protected in the core of the microcapsules for a defined period of time, and secondly are either gradually released through the membrane according to a certain release rate, or released in bulk in one go. In this case, the release is triggered by a process ensuring a specific release.

The problem that the present invention proposes to solve here is thus that of designing a physically and chemically stable composition capable of containing at least one irritant active ingredient, in particular a retinoid, for the treatment of dermatological pathologies, more particularly acne, said active ingredient being in dissolved form, the composition according to the invention making it possible to improve the tolerance of the active ingredient while at the same time being easy to use and being cosmetically acceptable for application to any area of the body that might be affected by the pathology.

According to the invention, the term "physical stability" is intended to mean a composition of which the physical properties such as the organoleptic properties, the microcapsule size, the pH and the viscosity are stable over time and under various temperature conditions: 4° C., ambient temperature, 40° C.

According to the invention, the term "chemical stability" refers to a composition in which the active ingredient is chemically stable over time, irrespective of the temperature condition: 4° C., ambient temperature, 40° C.

The term "ambient temperature" is intended to mean a temperature between 15 and 25° C.

According to the present invention, the irritant active ingredient, preferably the retinoid, must be in a dissolved form in a stable composition. For example, many retinoids often present solubilization difficulties. The retinoids according to the invention, and in particular the retinoid preferentially used, have low solubility, thus limiting their incorporation into the carriers cited in the preceding patents, and making it difficult to obtain a stable composition. Moreover, the addition of a solubilizer to topical formulations often increases the irritant power of the formulations.

In order to improve the tolerance of irritant active ingredients, in particular of retinoids, and the stability of the active agent in an aqueous formulation for cutaneous application, the Applicant has discovered, surprisingly, that a composition which can modify the structure of the interface between the active ingredient dissolution medium and the aqueous phase has an influence on the stability and the tolerance of the active ingredient in the composition. In the present invention, the active ingredient is dissolved in the oily core of lipid microcapsules.

The term "lipid microcapsules" is intended to mean a vesicular system of micrometric size, i.e. of size greater than one micrometer, consisting of a non-polymeric lipid shell surrounding an oily core that is liquid or semiliquid at ambient temperature.

The term "oily core" or "lipid internal phase" is intended to mean the internal phase of the lipid microcapsules of micrometric size containing a water-immiscible lipophilic solvent.

The present invention thus relates to the formulation of lipid microcapsules of micrometric size that can improve the cutaneous tolerance of irritant active ingredients, in particular retinoids, in the treatment of dermatological pathologies, in particular acne.

The oily core of the lipid microcapsules of micrometric size of the present invention is lipophilic, allowing the dissolution of hydrophobic active ingredients in larger amount.

The present invention is a system for using lipid microcapsules of micrometric size without the use of a volatile organic solvent often used for the formation of the shell, thus limiting the risks of toxicity and intolerance and in particular of irritation.

According to the present invention, the composition comprises lipid microcapsules of micrometric size and not lipid microspheres. In contrast, lipid microspheres are matrix particles, i.e. particles of which all of the mass is solid at ambient temperature. When microspheres contain a pharmaceutically acceptable active ingredient, it is finely dispersed or dissolved in the solid matrix. The lipid microcapsules of micrometric size according to the invention are particles of which the core is composed of one or more fatty substance(s) that is (are) liquid or semiliquid at ambient temperature, in which is preferentially the dissolved active ingredient, and the shell of which is lipid and non-polymeric in nature. Indeed, the lipid microcapsules of micrometric size according to the invention require no polymer and therefore no in situ polymerization.

The applicant has therefore, surprisingly, discovered lipid microcapsules of micrometric size which do not require the use of polymer or of volatile organic solvent, and which are capable of comprising at least one irritant active ingredient, preferably a retinoid, in dissolved form.

Thus, the lipid microcapsules of micrometric size make it possible to guarantee the stability of at least one irritant active ingredient, preferably a retinoid, in dissolved form in the lipid microcapsules, and also good tolerance of the composition obtained from these microcapsules.

The compositions according to the invention may also promote the cutaneous penetration of the active agent, which is useful in the treatment of dermatological complaints, in particular acne.

A first subject of the present invention is therefore a lipid microcapsule of micrometric size containing an oily internal phase and a non-polymeric shell obtained from at least one lipid compound chosen from amphiphilic lipids.

The lipid microcapsule of micrometric size according to the invention preferably contains an irritant active ingredient dissolved in the oily internal phase.

In other words, the lipid microcapsules of micrometric size according to the invention preferably consist of:
  a non-polymeric shell obtained from at least one lipid compound; and
  at least one oily core in which the retinoid is dissolved;
  at least one irritant active ingredient, preferably a retinoid.

The invention relates in particular to lipid microcapsules of micrometric size produced without volatile organic solvent.

A subject of the present invention is also a primary emulsion composed of lipid microcapsules of micrometric size dispersed in an aqueous phase.

The term "primary emulsion" is thus intended to mean the lipid system composed of the lipid microcapsules of micrometric size with a solid or semisolid interface, which are dispersed in a continuous aqueous phase, said microcapsules containing an oily core in which is preferentially the irritant active ingredient, and in particular the retinoid, which is dissolved, and a shell obtained from a lipid compound, forming the semisolid or solid interface between the oily internal phase and the continuous aqueous phase. This primary emulsion is therefore an oil-in-water emulsion.

Said oil-in-water primary emulsion according to the invention can be incorporated in a pharmaceutically acceptable carrier, such as a gel, a solution or an emulsion, for instance a cream or a lotion.

The present invention thus also relates to a composition, in particular a pharmaceutical composition, said composition comprising, in a pharmaceutically acceptable carrier, the primary emulsion according to the invention.

The present invention thus relates to a pharmaceutical composition, said composition comprising, in a pharmaceutically acceptable carrier, the primary emulsion composed of lipid microcapsules of micrometric size preferably consisting of:
  a non-polymeric shell obtained from at least one lipid compound;
  at least one oily core in which the retinoid is dissolved;
  at least one irritant active ingredient, preferably a retinoid,
  said lipid microcapsules of micrometric size being dispersed in an aqueous phase.

According to the invention, the term "composition" is thus intended to mean the primary emulsion, incorporated in a pharmaceutically acceptable carrier, such as an excipient or a mixture of excipients that can form a composition in the form of a gel, a solution or an emulsion, for instance a cream or a sprayable or non-sprayable lotion.

The compositions according to the invention have the advantage of being physically and chemically stable.

According to the present invention, the term "lipid microcapsules of micrometric size" is intended to mean lipid microsystems of which the size is preferentially between 1 µm and 100 µm.

According to one preferred embodiment, 50% of the lipid microcapsules have at least one mean size of between 1 and 80 µm and preferentially of between 1 and 50 µm. In one particularly preferred mode, the microcapsules according to the invention have a mean size of between 1 and 20 µm.

The lipid microcapsules of micrometric size are present in the composition according to the invention in an amount of between 0.1% and 30%, preferably between 0.5% and 20% and more particularly between 1% and 10% by weight relative to the total weight of the composition.

The microcapsules each consist of a core that is liquid or semiliquid at ambient temperature, preferably containing the active ingredient, and of a shell obtained from at least one lipid compound.

The prior art (U.S. Pat. No. 8,057,823, FR 2 805 761 and WO2011/036234) presents lipid capsules containing phosphatidylcholines, but said capsules are of nanometric size and, in order for them to be produced, require the systematic presence of at least one hydrophilic nonionic co-surfactant which is an oxyethylenated derivative of fatty alcohols and of fatty acids.

In contrast with the prior art, the present invention relates to lipid microcapsules of micrometric size containing exclusively phosphatidylcholines without any other additional lipophilic or hydrophilic co-surfactant.

The shell encapsulating the oily core that is liquid or semiliquid at ambient temperature is preferably composed of a non-polymeric material that is rigid at ambient temperature and the transition temperature or melting point of which is high. In order to be rigid at ambient temperature, the transition temperature or melting point must be greater than 35° C., preferably greater than 40° C. and ideally greater than 45° C.

In the microcapsules according to the invention, the shell consists of at least one lipid compound of amphiphilic type. Preferentially, the shell consists of only one lipid compound, advantageously chosen from amphiphilic lipids. More preferentially, the lipid compound is chosen from the family of phospholipids, and more specifically phosphatidylcholines or lecithins. Phosphatidylcholines or lecithins show good compatibility with the skin and have a very low irritant potential.

As lecithins that may be used, mention may be made in particular of natural or synthetic or derived soybean or egg lecithins. The first type of lecithin is phosphatidylcholine (PC). Other types of lecithin exist, including phosphatidylglycerol, phosphatidylinositol, sphingomyelin and phosphatidylethanolamine.

Among the lecithins with a transition temperature of greater than 35° C., mention may be made more particularly of dipalmitoylphosphatidylcholine (DPPC), distearoylphosphatidylcholine (DSPC), dibehenylphosphatidylcholine (DBPC), palmitoylstearoylphosphatidylcholine (PSPC), palmitoylbehenylphosphatidylcholine (PSPC) and stearoylbehenylphosphatidylcholine (SBPC), and also any saturated lecithins with long chains of fatty acids and derivatives thereof.

The lecithins in particular used in the present invention are solid at ambient temperature, which promotes the formation of a semisolid interface around the liquid or semiliquid core. This formulation allows the encapsulation of the active ingredient dissolved in the oily core, more particularly the retinoid.

The lipid microcapsules of micrometric size according to the invention more particularly contain a semisolid or solid interface between the internal phase and the aqueous continuous phase, by virtue of the use, as sole lipid compound, of a preferentially hydrogenated lecithin. More particularly, the hydrogenated lecithin used according to the invention has a high percentage of saturated phosphatidylcholine.

The term "high percentage" is intended to mean an amount of greater than 85% of hydrogenated (or saturated) phosphatidylcholine relative to the total weight of lecithin.

As lecithins preferentially used according to the invention, mention may be made of certain hydrogenated lecithins with a content of hydrogenated phosphatidylcholine of greater than 85%, for instance Lipoid® of grade P100-3, Phospholipon® of grade 90H sold by the company Lipoid, Epikuron® of grade 200 SH sold by Cargill, or Emulmetik® 950 sold by Lucas Meyer. Preferentially, the lecithin used as sole lipid compound is Phospholipon® 90H, for which the content of hydrogenated phosphatidylcholine is greater than 90% and the transition temperature of which is about 54° C.

The lipid compound surrounding the liquid or semiliquid core as defined above is present in an amount of between 0.01% and 10% by weight, preferably between 0.05% and 5% by weight and more preferentially between 0.1% and 1% by weight relative to the total weight of the microcapsule.

The lipid compound, in particular the hydrogenated lecithin, according to the invention enables by itself the encapsulation of the retinoid, which avoids contact of this active agent with the aqueous phase, and thus ensures its chemical stability. In particular, the lipid microcapsule, and in particular the shell, is free of any co-surfactant, in particular of lipophilic or hydrophilic co-surfactant.

The lipid microcapsules of micrometric size are in particular free of volatile organic solvent.

In particular, the lipid microcapsules of micrometric size are free of polymer.

The composition according to the invention thus preferably comprises in the microcapsules at least one active ingredient known to those skilled in the art as having an irritant nature. The irritant active ingredients that may preferentially be used according to the invention are retinoids. The retinoids that may be used in the context of the invention in particular comprise all-trans-retinoic acid or tretinoin, 13-cis-retinoic acid or isotretinoin, acitretin, arotinoic acid, retinol, adapalene, tazarotene, retinaldehyde, etretinate and the compounds protected in patent application WO 2006/066978 such as 3"-tert-butyl-4'-(2-hydroxyethoxy)-4"-pyrrolidin-1-yl-[1,1';3',1"]-terphenyl-4-carboxylic acid or Trifarotene, the compounds of patent application FR 0512367 including 2-hydroxy-4-[3-hydroxy-3-(5,6,7,8-tetrahydro-5,5,8,8-tetramethyl-2-naphthyl)-1-propynyl]benzoic acid or an enantiomer thereof, the compounds of patent application WO 05/56516 including 4'-(4-isopropylaminobutoxy)-3'-(5,5,8,8-tetramethyl-5,6,7,8-tetrahydronaphthalen-2-yl)-biphenyl-4-carboxylic acid, the compounds of patent application PCT/EP04/014809 including 4-{3-hydroxy-3-[4-(2-ethoxyethoxy)-5,5,8,8-tetramethyl-5,6,7,8-tetrahydronaphthalen-2-yl]-prop-1-ynyl}benzoic acid, and the compounds of patent application FR 2 861 069 including 4-[2-(3-tert-butyl-4-diethylaminophenyl)-2-hydroxyiminoethoxy]-2-hydroxybenzoic acid. 3"-tert-Butyl-4'-(2-hydroxyethoxy)-4"-pyrrolidin-1-yl-[1,1';3',1"]-terphenyl-4-carboxylic acid, as protected in patent application WO 2006/066978, is particularly preferred. In the rest of the present patent application, 3"-tert-butyl-4'-(2-hydroxyethoxy)-4"-pyrrolidin-1-yl-[1,1';3',1"]-terphenyl-4-carboxylic acid, the preferred compound according to the invention, will also be referred to as Trifarotene.

The composition according to the invention preferably comprises between 0.00001% and 1% and preferably from 0.0001% to 0.5% by weight of at least one retinoid relative to the total weight of the composition, and preferentially the composition according to the invention contains from 0.001% to 0.05% by weight of a retinoid relative to the total weight of the composition. In one preferred mode according to the invention, the composition comprises between 0.001% and 0.05% of Trifarotene, and more particularly between 0.003% and 0.03% by weight relative to the total weight of the composition.

The irritant active ingredient, in particular the retinoid, and more particularly the Trifarotene, is thus dissolved in the core of the lipid microcapsules of micrometric size according to the invention. Said core, or oily internal phase, comprises at least one fatty substance that is liquid or semiliquid at ambient temperature.

When the microcapsules contain at least one irritant active ingredient, then the composition of the internal phase of the microcapsules is essential for the stability of the active ingredient. The oily internal phase must, of course, be compatible with the active agent to be dissolved, and be able to dissolve the active agent when the latter is present in the microcapsules.

The term "phase that can dissolve the active agent" is intended to mean a phase in which the active ingredient is stable and has a solubility strictly greater than 0.1% by weight, in particular at ambient temperature.

For the purposes of the invention, the term "stability of the active ingredient in the oily phase" is intended to mean that the active ingredient is chemically stable over time regardless of the temperature condition: 4° C., ambient temperature, 40° C.

The stability of the active ingredient in the oily phase is in particular evaluated by liquid chromatography coupled to a UV detector (HPLC-UV).

For the purposes of the present invention, the term "fatty substance that is liquid or semiliquid at ambient temperature" is intended to mean an oily solvent.

The term "oily solvent" is intended to mean any water-immiscible material of natural, animal or synthetic origin, at ambient temperature.

This oily internal phase thus comprises at least one oily solvent, chosen from triglycerides and oils containing same, mineral oils, fatty acid esters, carboxylic acid esters, polyethoxylated fatty acids, fatty alcohols and corresponding esters, polyethylene glycol ethers, amides or glycols.

In one preferred mode according to the invention, the oily solvent constituting the oily internal phase does not comprise any fatty acids which are not esterified or polyethoxylated.

More particularly, the oily solvent may be a mineral oil, a triglyceride, a fatty acid ester, a carboxylic acid ester, a fatty alcohol, or a polyethylene glycol ether.

Among the mineral oils, mention may be made, in a nonlimiting manner, of liquid paraffin.

Among the triglycerides and oils containing the same, mention may be made, in a nonlimiting manner, of octanoic acid triglycerides or caprylic/capric acid triglycerides, such as those sold by the company Stéarineries Dubois or those sold under the names Miglyol® 810, 812 and 818 by the company Sasol.

Among the fatty acid esters, mention may be made, in a nonlimiting manner, of the diisopropyl adipate such as the commercial product Crodamol® DA sold by the company Croda or Schercemol DIA Ester® sold by the company Lubrizol, or cetearyl isononanoate sold under the name Cetiol SN® by the company BASF.

Among the carboxylic acid esters, mention may be made, in a nonlimiting manner, of ($C_{12-15}$) alkyl benzoate, such as the commercial product Crodamol® AB sold by the company Croda, or propylene glycol caprylate sold under the name Capryol 90® by the company Gattefossé.

Among the fatty alcohols, mention may be made in a nonlimiting manner of octyldodecanol or octyldodecanol octanoate.

Among the polyethylene glycol ethers, mention may be made in a nonlimiting manner of the PPG-15 stearyl ether sold under the name Arlamol PS11E-LQ by the company Croda.

In one preferred mode according to the invention, the solvents used in the oily internal phase are ($C_{12-15}$) alkyl benzoate, propylene glycol caprylate or caprylic/capric acid triglycerides.

In another preferred mode according to the invention, in the presence of an active ingredient, the preferred oily internal phase which is a solvent of the active ingredient is diisopropyl adipate or PPG-15 stearyl ether.

In particular, those skilled in the art will choose the suitable oily solvent(s) according to the irritant active ingredient to be dissolved.

According to one preferred embodiment, the oily solvents that are preferred for dissolving Trifarotene are diisopropyl adipate or PPG-15 stearyl ether.

Likewise, the oily internal phase may also contain one or more non-oily co-solvents or other co-solvents of nonvolatile organic type, in particular N-methyl-2-pyrrolidone or dimethylisosorbide or else dimethyl sulfoxide.

In one preferred mode according to the invention, the internal phase requires no solvents/co-solvent of alcoholic type in order to dissolve the active ingredient. The mixtures of solvents chosen according to the invention are sufficient to obtain the required solubility and stability of the active agent in the microcapsules without having recourse to any alcoholic solvent.

In addition to this or these oily solvent(s), the internal phase may also comprise one or more fatty substances that are liquid or semiliquid at ambient temperature and that cannot dissolve the active agent.

The term "fatty substance that cannot dissolve the active agent" is intended to mean a compound in which the active ingredient, preferably the retinoid, has a solubility of less than or equal to 0.1%.

In the oily internal phase, the solvent will be present in an amount of between 50% and 99.997% by weight relative to the total weight of the internal phase; preferably in an amount of between 70% and 99.997% and preferably between 95% and 99.997% by weight relative to the total weight of the internal phase.

In the oily internal phase, the optional co-solvent or fatty substance is present in an amount of between 0% and 50% by weight relative to the total weight of the internal phase; preferably in an amount of between 0.1% and 25% and preferably between 0.5% and 10% by weight relative to the total weight of the internal phase.

In addition to this or these oily solvent(s) and this or these fatty substance(s) which cannot dissolve the active agent, the internal phase may also comprise one or more compounds such as, for example, antioxidants or preservatives.

As previously indicated, the invention also relates to a primary emulsion composed of the lipid microcapsules of micrometric size dispersed in an aqueous phase, as described above.

Preferably, the emulsion of oil-in-water type according to the invention comprises lipid microcapsules of micrometric size as described above, preferably comprising an irritant active ingredient solubilized in the oily core.

In the primary emulsion according to the invention, the oily internal phase of the microcapsules is present in an amount of between 0.1% and 50% by weight relative to the total weight of the primary emulsion, preferably in an amount of between 0.5% and 35% by weight relative to the total weight of the primary emulsion.

In the primary emulsion according to the invention, the ratio between the internal oily phase and the amount of hydrogenated lecithin is between 5 and 10 to 1. Preferably, this ratio in the emulsion is between 6 and 8 to 1 and preferentially 7 to 1.

Moreover, the ratio between the water and the internal oily phase is between 1.25 and 5 to 1. Preferably, this ratio between the water and the internal oily phase is between 2 and 4 to 1 and preferentially 2 and 3 to 1.

In the primary emulsion, the microcapsules are dispersed in an aqueous phase. The continuous aqueous phase comprises water. This water may be demineralized water, a floral water, or a natural spring or mineral water.

The water may be present in a content of between 55% and 95% by weight relative to the total weight of the composition, preferably of between 60% and 95% by weight.

A subject of the present invention is thus a composition, in particular a pharmaceutical composition, said composition comprising the primary emulsion containing the lipid microcapsules of micrometric size defined above in the text of the present invention in a pharmaceutically acceptable carrier, such as a gel, a solution or an emulsion, for instance a cream or a lotion.

When the pharmaceutically acceptable carrier is a gel, the primary emulsion is dispersed in an aqueous phase which comprises at least one gelling agent. This gelling agent may be a cellulose-based derivative chosen from semisynthetic cellulose-based gelling agents.

The gelling agent may also be chosen from natural gums, in particular xanthan gum (known for example under the name Satiaxane and sold by the company Cargill), starch and derivatives thereof, crosslinked polyacrylic acid polymers, for instance carbomers, such as Carbopol 980 or Carbopol Ultrez 10 and from alkyl derivatives thereof, for instance copolymers of acrylates/C10-30 alkyl acrylate, such as Carbopol ETD2020, Pemulen TR1, Pemulen TR2, carboxyvinyl polymers, polyvinylpyrrolidones and derivatives thereof, and polyvinyl alcohols. The gelling agent may also be chosen from emulsifying polymers such as Sepigel 305 consisting of a polyacrylamide/C13-C14 isoparaffin/laureth-7 mixture, or Simulgel® 600PHA or Sepineo® P600, namely sodium acryloyldimethyltaurate copolymer/isohexadecane/polysorbate 80. These two products are sold by the company SEPPIC.

When the pharmaceutically acceptable carrier is a solution, the primary emulsion is dispersed in a carrier composed of an aqueous phase.

The term "aqueous phase which constitutes the pharmaceutically acceptable carrier" is intended to mean any aqueous phase as defined previously in the present invention.

When the pharmaceutically acceptable carrier is a cream or a lotion, the primary emulsion is dispersed in a carrier composed of an aqueous phase and of a fatty phase optionally comprising at least one surfactant or emulsifier.

In the case of pharmaceutical carriers in cream or lotion form, the composition according to the invention thus comprises a fatty phase. This fatty phase may comprise, for example, vegetable oils, mineral oils, animal oils, synthetic oils or silicone oils, and mixtures thereof.

Preferably, when the carrier of the composition according to the invention is a cream or lotion, the emulsion is in the form of an oil-in-water (O/W) emulsion. This emulsion may or may not comprise at least one emulsifier.

The cream or lotion according to the invention also comprises an aqueous phase.

The term "aqueous phase which constitutes the pharmaceutically acceptable carrier, alone or in an emulsion" is intended to mean any aqueous phase as defined previously in the present invention.

The composition according to the invention may also contain, in the primary emulsion or the pharmaceutically acceptable carrier, additives or combinations of additives, such as:
preservatives;
pro-penetrants;
stabilizers;
humectants;
humidity regulators;
pH regulators;
osmotic pressure modifiers;
chelating agents;
UV-A and UV-B screening agents;
and antioxidants.

Needless to say, those skilled in the art will take care to select the ingredients of the pharmaceutically acceptable carrier and in particular the aqueous phases, the fatty phases, the emulsifiers and also the optional compound(s) to be added to these compositions such that the advantageous properties intrinsically associated with the present invention are not, or are not substantially, adversely affected by the choice of the ingredients.

The composition according to the invention thus comprises, in a pharmaceutically acceptable carrier, on a weight basis relative to the total weight of the composition, microcapsules composed of:
a) a non-polymeric shell obtained from 0.01% to 10% of lipid compound chosen from amphiphilic lipids;
b) an oily core composed of from 0.1% to 50% of fatty substance that is liquid or semiliquid at ambient temperature;
c) 0.00001% to 0.3% of at least one retinoid.

The composition according to the invention thus preferably comprises, in a pharmaceutically acceptable carrier, on a weight basis relative to the total weight of the composition, microcapsules composed of:
a) 0.1% to 5% of lipid compound chosen from amphiphilic lipids, preferably hydrogenated lecithin;
b) 1% to 30% of fatty substance that is liquid or semiliquid at ambient temperature, preferably fatty acid esters or polyethylene glycol ethers;
c) between 0.00001% and 0.1% of at least one retinoid, preferably Trifarotene.

In accordance with this preferred embodiment, the composition may comprise from 1% to 20% by weight of fatty substance that is liquid or semiliquid at ambient temperature, preferably fatty acid esters or polyethylene glycol ethers.

In a preferred embodiment according to the invention, the composition comprises, in a pharmaceutically acceptable carrier, on a weight basis relative to the total weight of the composition:
a) 0.1% to 5%, in particular from 0.1% to 1%, of hydrogenated lecithin with a hydrogenated phosphatidylcholine content of greater than 85%;
b) 1% to 30%, in particular from 1% to 5%, of fatty acid esters or of polyethylene glycol ethers;
C) 0.001% to 0.03% of Trifarotene.

The pharmaceutical composition that may be used according to the invention is intended for treating the skin and may be administered topically, parenterally or orally.

Via the oral route, the pharmaceutical composition may be in liquid or pasty form, and more particularly in the form of gel capsules, coated tablets or syrups.

Via the parenteral route, the composition may be in the form of suspensions for perfusion or for injection.

Preferably, the composition is in a form suitable for topical administration. The term "via the topical route" is intended to mean application to the skin, the mucous membranes, the hair or the scalp.

Via the topical route, the composition may be in liquid or pasty form, and more particularly in the form of creams, milks, pomades, impregnated pads, syndets, wipes, gels, sprays, foams, lotions, sticks, shampoos or washing bases.

A subject of the invention is also a process for preparing the compositions according to the invention. Preferably, a subject of the invention is the process for preparing the compositions comprising at least one retinoid, preferably Trifarotene.

The process according to the invention does not involve phase inversion phenomena characterized by a phase inversion temperature (PIT) (used in particular in patents FR 2 805 761 and FR 2 840 531), and therefore does not require temperature increase and decrease cycles.

The process according to the invention does not use a high pressure homogenizer (HPH) and does not therefore require a pre-homogenization step.

The process according to the invention therefore has the advantage of at the same time not having successive heating and cooling cycles, not using volatile organic solvent and polymer, and not requiring an emulsion gelling step or a pre-homogenization step.

The process as presented according to the invention and proposed for producing the lipid microcapsules of micrometric size as described above uses equipment which allows high-shear emulsification.

Various devices can be used, for instance high-shear rotor/stator type mixers, such as a Polytron (Kinematica) or the Magic Lab (Ika). In a manner likewise alternative to the rotor/stator, sonication may be used with, for example, a Branson probe. Whatever the type of equipment used, the process consists in producing a primary emulsion, which is then diluted in a pharmaceutically acceptable carrier.

This primary emulsion makes it possible to vary the mode of introduction of the hydrogenated lecithin, which can be totally introduced into the oily phase (100% oily phase) or into the aqueous phase (100% aqueous phase) or introduced in various ratios, for instance a 50/50 ratio, into the oily phase and into the aqueous phase.

1—Preparation of the Primary Emulsion:
The production of the primary emulsion comprises 3 steps:
  Preparation of the aqueous phase
  Preparation of the oily phase
  Mixing of the aqueous and oily phases.

The preparation of the aqueous phase and the preparation of the oily phase may be dependent on the choice of the mode of dispersion of the hydrogenated lecithin:
  100% in aqueous phase or
  100% in oily phase or
  50/50% aqueous phase/oily phase.

a) Preparation of the primary emulsion with 100% dispersion of the lipid compound, preferably of the hydrogenated lecithin, in the aqueous phase:
Preparation of the Aqueous Phase:
In a container suitable for containing all of the primary emulsion, the lipid compound, preferably the hydrogenated lecithin, used is dispersed in all of the aqueous phase heated to approximately 75° C., using a high shear rotor/stator type mixer such as an Ultra Turrax (Ika), a Polytron (Kinematica) or the Magic Lab (Ika), with stirring between 5000 and 10 000 rpm, for a defined period of time which will not exceed 30 minutes. A preservative and an antioxidant may be added to this phase.
Preparation of the Oily Phase:
The active ingredient, if present, is dissolved in the internal oily phase heated to approximately 75° C., comprising, inter alia, the oil for dissolving the active ingredient, in a suitable container and using a magnetic bar. A preservative and an antioxidant may be added to this phase after the active ingredient has been dissolved.

b) Preparation of the primary emulsion with 100% dispersion of the lipid compound, preferably of the hydrogenated lecithin, in the oily phase:
Preparation of the Aqueous Phase:
All of the aqueous phase is heated to 75° C. in a container suitable for containing all of the primary emulsion. A preservative and an antioxidant may be added to this phase.
Preparation of the Oily Phase:
The active ingredient, if present, is dissolved in the internal oily phase heated to approximately 75° C., comprising, inter alia, the oil for dissolving the active ingredient, in a suitable container and using a magnetic bar. A preservative and an antioxidant may be added to this phase after the active ingredient has been dissolved. The lipid compound, preferably the hydrogenated lecithin, used is dispersed in this oily phase still at approximately 75° C., using a high shear rotor/stator type mixer such as an Ultra Turrax (Ika) or a Polytron (Kinematica), with stirring between 5000 and 10 000 rpm, for a defined period of time which will not exceed 30 minutes.

c) Preparation of the primary emulsion with 50% of the lipid compound, preferably of the hydrogenated lecithin, dispersed in the aqueous phase and 50% in the oily phase:
Preparation of the Aqueous Phase:
In a container suitable for containing all of the primary emulsion, all of the aqueous phase is heated to 75° C. Approximately half the lipid compound, preferably the hydrogenated lecithin, used is dispersed in this aqueous phase still heated to approximately 75° C., using a high shear rotor/stator type mixer such as an Ultra Turrax (Ika), a Polytron (Kinematica) or the Magic Lab (Ika), with stirring between 5000 and 10 000 rpm, for a defined period of time which will not exceed 30 minutes. A preservative and an antioxidant may be added to this phase.
Preparation of the Oily Phase:
The active ingredient, if present, is dissolved in the internal oily phase heated to approximately 75° C., comprising, inter alia, the oil for dissolving the active ingredient, in a suitable container and using a magnetic bar. The other portion of the lipid compound, preferably of the hydrogenated lecithin, is dispersed in this oily phase still heated to approximately 75° C., using a high shear rotor/stator type mixer such as an Ultra Turrax (Ika) or a Polytron (Kinematica), with stirring between 5000 and 10 000 rpm, for a defined period of time which will not exceed 30 minutes. A preservative and an antioxidant may be added to this phase after the active ingredient has been dissolved.

Once the aqueous and oily phases have been prepared, they are mixed by incorporation of the oily phase into the aqueous phase. The procedure is dependent on the type of apparatus used. Three types of apparatus are preferentially used for mixing the two phases resulting in the primary emulsion according to the invention: the process with a Polytron, the process with a Magic Lab and the process with a sonication probe. According to the various types of stirrers, the emulsion is produced as described:
  Process with a Polytron with temperature regulation at 75° C.:
  Incorporation of the oily phase onto the aqueous phase gently, with stirring between 5000 and 10 000 rpm.
  Once the incorporation has been achieved, stirring at a higher speed for a minimum of 30 minutes.
  Process with a Magic Lab with temperature regulation at 75° C.:
  Simultaneous incorporation of the aqueous phase and of the oily phase in the apparatus with stirring at a speed of less than 16 000 rpm if the lipid compound, preferably hydrogenated lecithin, was 100% dispersed in the fatty phase.

Incorporation of the oily phase onto the aqueous phase already present in the apparatus with stirring at a speed of less than 16 000 rpm if the lipid compound, preferably hydrogenated lecithin, was 100% dispersed in the aqueous phase.

Once the incorporation has been achieved, allow the mixture to circulate until it returns to ambient temperature.

Process with the sonication probe with temperature regulation fixed below 50° C.:

Incorporation of the oily phase onto the aqueous phase rapidly, at an ultrasound amplitude fixed at 80 microns, leave the mixture under these conditions for several tens of seconds.

2—Preparation of the Final Composition According to the Invention

The primary emulsion previously obtained is then introduced into a previously prepared pharmaceutically acceptable carrier, of solution, cream, lotion or gel type.

In the case of a gel containing mainly only water and a gelling agent, the gelling step is carried out instantaneously at the end of the production of the primary emulsion:

Remove a predetermined amount of primary emulsion and

Incorporate it gently into a previously prepared gel, with gentle stirring.

The stirring can be generated using a deflocculating paddle attached to a stirring motor of IKA or Rayneri type. Gentle stirring corresponds to a speed which makes it possible to obtain a homogeneous gel after 20 minutes without generating excessive aeration of the formulation, for example a speed around 200 rpm.

Alternatively, to prepare a composition of gel type according to the invention, an amount of primary emulsion may be removed and then diluted in one part of water. This mixture is then thickened by adding a gelling agent.

The process for preparing the compositions according to the invention comprises the following steps:

(i) preparation of the primary emulsion by:

(a) dissolution of the active ingredient if present in a fatty substance that is liquid or semiliquid at ambient temperature, to obtain the oily phase;

(b) preparation of the aqueous phase;

(c) dispersion of the lipid compound in the oily phase obtained in (a) or in the aqueous phase obtained in (b) or partly in each of the oily and aqueous phases;

(d) heating of the two oily and aqueous phases separately to about 75° C.;

(e) mixing with stirring of the oily and aqueous phases obtained at the end of step (d);

(ii) incorporation of the composition obtained in the preceding step into a pharmaceutically acceptable carrier.

Thus, the Applicant has discovered, surprisingly, that the mode of introduction of the lipid compound, and more particularly of the hydrogenated lecithin, has an influence on the stability over time of the microcapsules dispersed in the pharmaceutically acceptable carrier.

In accordance with the present invention, the microcapsules and processes making it possible to obtain them, as described above, have the advantage compared with the prior art of using alternative processes to the processes that use temperature increase and decrease cycles or high-pressure homogenizers.

Preferably, the lipid compound is introduced either 100% into the oily phase, or 100% into the aqueous phase, depending on the nature of the oily core chosen in order to dissolve therein the active ingredient, in particular Trifarotene, within the microcapsule.

More preferentially, the hydrogenated lecithin is introduced either 100% into the oily phase, or 100% into the aqueous phase, depending on the nature of the oily core chosen in order to dissolve therein the Trifarotene within the microcapsule.

In one preferred mode according to the invention, the preferred apparatus is the Magic Lab.

In one preferred mode according to the invention, the preferred mode of dispersion of the lipid compound, and more preferentially of the hydrogenated lecithin, is 100% in the fatty phase, in the case of the use of oily solvents of acid ester and triglyceride type, for instance diisopropyl adipate.

In another preferred mode according to the invention, the preferred mode of dispersion of the lipid compound, and more preferentially of the hydrogenated lecithin, is 100% in the aqueous phase, in particular in the case of the use of oily solvents of polyethylene glycol ether type, for instance PPG-15 stearyl ether.

In particular, those skilled in the art will choose the suitable oily solvent(s) according to the irritant active ingredient to be dissolved when the latter is present and thus the mode of dispersion of the lipid compound.

In one of the preferred modes, the process for preparing a composition according to the invention comprises the following steps:

(i) preparation of the primary emulsion by:

a) dissolution of the active ingredient if present in the internal oily phase or oily core and dispersion of the lipid compound, in particular the hydrogenated lecithin, in this same oily phase heated to 75° C.;

b) preparation of the aqueous phase, heated to 75° C.;

c) simultaneous incorporation of the aqueous phase and of the oily phase in the apparatus with stirring at a speed of less than 16 000 rpm;

d) once the incorporation has been achieved, allow the mixture to circulate until it returns to ambient temperature;

(ii) incorporation of the primary emulsion into the pharmaceutically acceptable carrier.

In one of the preferred modes, the process for preparing a composition according to the invention comprises the following steps:

(i) preparation of the primary emulsion by:

a) dissolution of the active ingredient if present in the internal oily phase or oily core heated to 75° C.;

b) dispersion of the lipid compound, in particular of the hydrogenated lecithin, in the aqueous phase, heated to 75° C.;

c) incorporation of the oily phase onto the aqueous phase already present in the apparatus with stirring at a speed of less than 16 000 rpm;

d) once the incorporation has been achieved, allow the mixture to circulate until it returns to ambient temperature;

(ii) incorporation of the primary emulsion into the pharmaceutically acceptable carrier.

Preferably, these preparation processes are carried out in the absence of volatile organic solvent.

The composition according to the invention may be used as a medicament.

In particular, a subject of the invention is also the composition as previously defined, for use thereof for treating dermatological complaints, in particular human complaints, as defined below:

1) dermatological complaints associated with a keratinization disorder relating to cell differentiation and proliferation, in particular for treating common acne, comedonal acne, polymorphic acne, acne rosacea, nodulocystic acne, acne conglobata, senile acne, secondary acne such as solar acne, acne medicamentosa or occupational acne;

2) keratinization disorders, in particular ichthyoses, ichthyosiform conditions, lamellar ichthyoses, Darier's disease, palmoplantar keratoderma, leukoplakia, pityriasis rubra pilaris and leukoplakiform conditions, cutaneous or mucosal (buccal) lichen;

3) dermatological complaints with an inflammatory immuno-allergic component, with or without a cell proliferation disorder, and in particular all forms of psoriasis, whether cutaneous, mucosal or ungual, and even psoriatic arthritis, or else atopic dermatitis and the various forms of eczema;

4) skin disorders caused by exposure to UV radiation, and also for repairing or combating skin aging, whether it is photo-induced or chronological, or for reducing actinic keratoses and pigmentations, or any pathological conditions associated with chronological or actinic aging, such as xerosis, pigmentations and wrinkles;

5) any condition associated with benign dermal or epidermal proliferations, whether or not they are of viral origin, such as common warts, flat warts, molluscum contagiosum and epidermodysplasia verruciformis, or oral or florid papillomatoses;

6) dermatological disorders such as immune dermatoses, for instance lupus erythematosus, bullous immune diseases and collagen diseases, such as scleroderma;

7) stigmata of epidermal and/or dermal atrophy induced by local or systemic corticosteroids, or any other form of cutaneous atrophy;

8) cicatrization disorders, or for preventing or repairing stretch marks, or else for promoting cicatrization;

Preferentially, the invention relates to the composition for use thereof in the treatment of acne, ichthyoses, ichthyosiform conditions, palmoplantar hyperkeratosis or psoriasis.

In other words, the invention relates to the composition according to the invention for use thereof as a medicament in the treatment of dermatological complaints, in particular human complaints, as previously defined.

In a particularly preferred manner, the composition according to the invention will comprise Trifarotene for treating acne, ichthyoses, ichthyosiform conditions, palmoplantar hyperkeratosis or psoriasis.

In particular, the invention relates to the use of the composition according to the invention for the treatment of dermatological complaints, in particular human complaints, as previously defined. In particular, the composition is used for the treatment of acne, ichthyoses, ichthyosiform conditions, palmoplantar hyperkeratosis or psoriasis.

Various composition formulations comprising a retinoid will now be given, as illustrations and with no limiting nature.

EXAMPLE 1

Solubility Data for Trifarotene in Various Oily Phases

The object of this preformulation study is to identify dissolving oily phases in which Trifarotene has a solubility of greater than 0.1% w/w and in which it is chemically stable.

The stability of the active agent was evaluated by liquid chromatography coupled to a UV detector (HPLC-UV).

| INCI name (trade name) | Maximum solubility (% w/w) | Stability |
|---|---|---|
| Propylene glycol monocaprylate (Capryol ® 90) | 0.802 | 6 months AT/40° C. |
| Propylene glycol monolaurate (Lauroglycol ® FCC) | 0.296 | 6 months AT/40° C. |
| Diisopropyl adipate (Schercemol Dia Ester) | 0.297 | 6 months AT/40° C. |
| PPG-15 stearyl ether (Arlamol PS11E-LQ) | 0.292 | 6 months AT/40° C. |
| Macrogol oleate (Labrafil ® M1944CS) | 0.156 | 6 months AT/40° C. |
| Octyldodecanol (Eutanol ® G) | 0.137 | Unstable |
| Propylene glycol dicaprylate/dicaprate (Myritol ® PC) | 0.069 | Unstable |
| Alkyl (C12-15) benzoate (Crodamol AB) | 0.026 | Not monitored |
| Caprylic/capric acid triglycerides (Miglyol ® 812N) | 0.019 | 6 months AT/40° C. |
| Sweet almond oil | 0.011 | 6 months AT/40° C. |
| Mineral oil | 0.0001 | Not monitored |

9) in the treatment of any complaint of fungal origin at the cutaneous level, such as tinea pedis and tinea versicolor;

10) pigmentation disorders, such as hyperpigmentation, melasma, hypopigmentation or vitiligo;

11) cutaneous or mucosal cancerous or precancerous conditions, such as actinic keratoses, Bowen's disease, in-situ carcinomas, keratoacanthomas and skin cancers such as basal cell carcinoma (BCC), squamous cell carcinoma (SCC) and cutaneous lymphomas such as T lymphoma.

AT Ambient Temperature

Following the results of this solubility and stability study, it is noted that propylene glycol monocaprylate, propylene glycol monolaurate, diisopropyl adipate, PPG-15 stearyl ether and macrogol oleate are suitable for dissolving Trifarotene.

Following these results, diisopropyl adipate and PPG-15 stearyl ether are preferred solvents for obtaining the desired concentrations of Trifarotene in the pharmaceutically acceptable carrier.

EXAMPLE 2

Compositions of Primary Emulsions a to G Containing the Placebo Lipid Microcapsules Before Dilution in a Pharmaceutically Acceptable Carrier By using the preparation processes previously mentioned and according to the mode of dispersion of the hydrogenated lecithin as previously defined in the present description, lipid microcapsules were prepared with an oily core containing an oil or a mixture of oils.

The compositions of the primary emulsions A to G containing such microcapsules are therefore the following:

| Ingredients | Composition (% w/w) | | | | | | |
|---|---|---|---|---|---|---|---|
| | A | B | C | D | E | F | G |
| Diisopropyl adipate | 27.89 | 27.89 | 27.89 | — | — | — | — |
| PPG-15 stearyl ether | — | — | — | 27.89 | — | — | — |
| Capric/caprylic acid triglycerides | — | — | — | — | 27.89 | — | 17.89 |
| Alkyl (C12-15) benzoate | — | — | — | — | — | 27.89 | — |
| Propylene glycol caprylate | — | — | — | — | — | — | 10 |
| Hydrogenated lecithin | 4.04 | 4.04 | 4.04 | 4.04 | 4.04 | 4.04 | 4.04 |
| Propyl paraben | 0.56 | 0.28 | 0.14 | 0.56 | 0.56 | 0.56 | 0.56 |
| Methyl paraben | 1.12 | 0.56 | 0.28 | 1.12 | 1.12 | 1.12 | 1.12 |
| Purified water | Qs 100 | Qs 100 | Qs 100 | Qs 100 | Qs 100 | Qs 100 | Qs 100 |

EXAMPLE 3

Compositions of Primary Emulsions A1 and B1 Containing the Lipid Microcapsules Comprising Trifarotene Before Dilution in a Pharmaceutically Acceptable Carrier By using the processes previously mentioned and according to the hydrogenated lecithin dispersion mode as previously defined in the present description, lipid microcapsules were prepared and contain in the oily core Trifarotene dissolved in a solvent oil or a mixture of solvent oils.

The primary emulsions were prepared preferentially using, as solvent for the Trifarotene, either diisopropyl adipate or PPG-15 stearyl ether.

The compositions of the primary emulsions A1 and B1 are therefore the following:

| Ingredients | Composition (% w/w) | |
|---|---|---|
| | A1 | B1 |
| Trifarotene | 0.056 | 0.056 |
| Diisopropyl adipate | 27.89 | — |
| PPG-15 stearyl ether | — | 27.89 |
| Hydrogenated lecithin | 4.04 | 4.04 |
| Propyl paraben | 0.56 | 0.56 |
| Methyl paraben | 1.12 | 1.12 |
| Purified water | Qs 100 | Qs 100 |

EXAMPLE 4

Characterization of the Primary Emulsion of Composition A1 of Example 3, Containing Trifarotene, Obtained According to the Three Processes and with the Various Modes of Dispersion of the Hydrogenated Lecithin The macroscopic observation is performed on the formulation in its original packaging.

| Equipment | Hydrogenated lecithin dispersion mode | Macroscopic observation of the primary emulsion |
|---|---|---|
| Polytron | 100% fatty phase | Liquid white |
| Magic Lab | 100% fatty phase | Liquid white |
| | 100% aqueous phase | Liquid white |
| Sonication | 100% fatty phase | Liquid white |

Whatever the type of equipment, with the hydrogenated lecithin 100% dispersed in the fatty phase, the primary emulsions A1 obtained have the same appearance.

In particular, with the Magic Lab, the primary emulsions A1 obtained have the same appearance as the mode of dispersion of the hydrogenated lecithin either 100% in the aqueous phase or 100% in the oily phase.

EXAMPLE 5

Characterization of the Particle Size Distribution of the Primary Emulsion of Composition A1 of Example 3, Containing Trifarotene, Obtained with the Magic Lab In the following example, the primary emulsions A1 were prepared with the Magic Lab by dispersing the hydrogenated lecithin either 100% in the aqueous phase or 100% in the fatty phase.

The particle size distribution of the lipid microcapsules in the primary emulsion A1 was determined using a Mastersizer 3000 particle size analyzer (Malvern). The composition is prediluted before analysis (1 g in 9 g of purified water). Five successive measurements are carried out on the same preparation.

The particle size distribution by volume is presented by expressing $D_{10}$, $D_{50}$ and $D_{90}$:

$D_{10}$ corresponds to the size of the particles below which is 10% of the sample, $D_{50}$ corresponds to the size of the particles below which is 50% of the sample, $D_{90}$ corresponds to the size of the particles below which is 90% of the sample.

The results obtained are as follows:

| Characterization | Hydrogenated lecithin dispersion mode | |
|---|---|---|
| | 100% aqueous phase | 100% fatty phase |
| $D_{10}$ (μm) | | |
| MEAN | 2.1 | 2.8 |
| STANDARD DEVIATION | 0.06 | 0.03 |
| $D_{50}$ (μm) | | |
| MEAN | 11 | 9 |
| STANDARD DEVIATION | 0.99 | 0.12 |
| $D_{90}$ (μm) | | |
| MEAN | 64 | 25 |
| STANDARD DEVIATION | 7.3 | 0.29 |

The data show that the lipid microcapsules obtained have a size greater than 1 micrometer.

EXAMPLE 6

Examples of Compositions of Gel Type According to the Invention Prepared from the Placebo Primary Emulsions of Compositions A to E of Example 2

In order to prepare compositions of gel type $I_G$ to $XVI_G$ according to the invention, various amounts of primary emulsions prepared according to example 2 were taken and diluted in a gel base.

To obtain a gel of 100 grams (gels $I_G$ and $IV_G$ to $XVI_G$) comprising approximately 5% of encapsulated oil, 17.784 grams of the placebo primary emulsion of compositions respectively A, D and E of example 2 are added to the formulation.

To obtain a gel of 100 grams (gel $II_G$) comprising 10% of encapsulated oil, 35.855 grams of the placebo primary emulsion of composition B of example 2 are added to the formulation.

To obtain a gel of 100 grams (gel $III_G$) comprising 20% of encapsulated oil, 71.71 grams of the placebo primary emulsion of composition C of example 2 are added to the formulation.

Examples of compositions of gel type obtained according to the invention are thus as follows:

| Ingredients | Compositions (% w/w) | | | | | | | |
|---|---|---|---|---|---|---|---|---|
| | $I_G$ | $II_G$ | $III_G$ | $IV_G$ | $V_G$ | $VI_G$ | $VII_G$ | $VIII_G$ |
| Diisopropyl adipate | 4.96 | 10 | 20 | — | — | 4.96 | — | — |
| PPG-15 stearyl ether | — | — | — | 4.96 | — | — | 4.96 | — |
| Capric/caprylic acid triglycerides | — | — | — | — | 4.96 | — | — | 4.96 |
| Hydrogenated lecithin | 0.72 | 1.4 | 2.90 | 0.72 | 0.72 | 0.72 | 0.72 | 0.72 |
| Methyl paraben | 0.2 | 0.2 | 0.2 | 0.2 | 0.2 | 0.2 | 0.2 | 0.2 |
| Propyl paraben | 0.1 | 0.1 | 0.1 | 0.1 | 0.1 | 0.1 | 0.1 | 0.1 |
| Sodium acryloyldimethyltaurate copolymer/ isohexadecane/ polysorbate 80 | 2 | 2 | 4 | 2 | 2 | 4 | 4 | 4 |
| Sodium docusate | — | — | — | — | — | 0.05 | 0.05 | 0.05 |
| Disodium edetate | — | — | — | — | — | 0.1 | 0.1 | 0.1 |
| Glycerol | — | — | — | — | — | 4 | 4 | 4 |
| Propylene glycol | — | — | — | — | — | 4 | 4 | 4 |
| Poloxamer P124 | — | — | — | — | — | 0.2 | 0.2 | 0.2 |
| Lactic acid (qs pH 3.5-4) | — | — | — | — | — | Qs pH | Qs pH | Qs pH |
| Purified water | Qs 100 | Qs 100 | Qs 100 | Qs 100 | Qs 100 | Qs 100 | Qs 100 | Qs 100 |

| Ingredients | Compositions (% w/w) | | | | | | | |
|---|---|---|---|---|---|---|---|---|
| | $IX_G$ | $X_G$ | $XI_G$ | $XII_G$ | $XIII_G$ | $XIV_G$ | $XV_G$ | $XVI_G$ |
| Diisopropyl adipate | 4.96 | 4.96 | 4.96 | 4.96 | — | — | — | — |
| PPG-15 stearyl ether | — | — | — | — | 4.96 | 4.96 | 4.96 | 4.96 |
| Hydrogenated lecithin | 0.72 | 0.72 | 0.72 | 0.72 | 0.72 | 0.72 | 0.72 | 0.72 |
| Methyl paraben | 0.2 | 0.2 | 0.2 | 0.2 | 0.2 | 0.2 | 0.2 | 0.2 |
| Propyl paraben | 0.1 | 0.1 | 0.1 | 0.1 | 0.1 | 0.1 | 0.1 | 0.1 |
| Sodium hydroxide (qs pH 4.5-5) | Qs pH | Qs pH | Qs pH | Qs pH | Qs pH | Qs pH | Qs pH | Qs pH |
| Carbomer | 0.5 | 0.7 | — | — | 0.5 | 0.7 | — | — |
| Crosslinked copolymer Acrylates/alkyl ($C_{10-30}$) Acrylate | — | — | 0.7 | 1 | — | — | 0.7 | 1 |
| Purified water | Qs 100 | Qs 100 | Qs 100 | Qs 100 | Qs 100 | Qs 100 | Qs 100 | Qs 100 |

EXAMPLE 7

Examples of Compositions of Gel Type According to the Invention Prepared from the Primary Emulsions of Example 3 Containing Trifarotene In order to prepare compositions of gel type $I_G'$ to $IV_G'$ according to the invention, an amount of corresponding primary emulsion prepared according to example 3 was taken and diluted in a gel base.

To obtain a gel of 100 grams containing 0.01% of Trifarotene, contained in the presence of approximately 5% of solvent oil in the microcapsules, 17.784 grams of the primary emulsion A1 or B1 of example 3 are added to the formulation.

Examples of compositions of gel type obtained according to the invention are thus as follows:

| Ingredients | Composition (% w/w) | | | |
| --- | --- | --- | --- | --- |
|  | $I_G'$ | $II_G'$ | $III_G'$ | $IV_G'$ |
| Trifarotene | 0.01 | 0.01 | 0.01 | 0.01 |
| Diisopropyl adipate | 4.96 | — | 4.96 | — |
| PPG-15 stearyl ether | — | 4.96 | — | 4.96 |
| Hydrogenated lecithin | 0.72 | 0.72 | 0.72 | 0.72 |
| Methyl paraben | 0.2 | 0.2 | 0.2 | 0.2 |
| Propyl paraben | 0.1 | 0.1 | 0.1 | 0.1 |
| Sodium acryloyldimethyltaurate copolymer/isohexadecane/polysorbate 80 | 2 | 2 | 2 | 2 |
| Sodium docusate | — | — | 0.05 | 0.05 |
| Disodium edetate | — | — | 0.1 | 0.1 |
| Glycerol | — | — | 4.0 | 4.0 |
| Propylene glycol | — | — | 4 | 4 |
| Poloxamer P124 | — | — | 0.2 | 0.2 |
| Lactic acid (qs pH 3.5-4) | — | — | Qs pH | Qs pH |
| Purified water | Qs 100 | Qs 100 | Qs 100 | Qs 100 |

EXAMPLE 8

Examples of Compositions of Formulations of Cream Type According to the Invention Prepared from the Placebo Primary Emulsions of Compositions A, D and E of Example 2

In order to prepare compositions of cream type according to the invention $I_C$ to $III_C$, an amount of corresponding primary emulsion prepared according to example 2 was taken and integrated at a predetermined moment during the process for preparing a cream.

To obtain a cream of 100 grams comprising approximately 5% of encapsulated oil, 17.784 grams of the primary emulsion of compositions respectively A, D and E of example 2 are added to the formulation.

Examples of compositions of cream type $I_C$ to $III_C$ obtained according to the invention are thus as follows:

| Ingredients | Compositions (% w/w) | | |
| --- | --- | --- | --- |
|  | $I_C$ | $II_C$ | $III_C$ |
| Diisopropyl adipate | 4.96 | — | — |
| PPG-15 stearyl ether | — | 4.96 | — |
| Capric/caprylic acid triglycerides | — | — | 4.96 |
| Hydrogenated lecithin | 0.72 | 0.72 | 0.72 |
| Methyl paraben | 0.2 | 0.2 | 0.2 |
| Propyl paraben | 0.1 | 0.1 | 0.1 |
| Sodium acryloyldimethyltaurate copolymer/isohexadecane/polysorbate 80 | 4 | 4 | 4 |
| Sodium docusate | 0.05 | 0.05 | 0.05 |
| Disodium edetate | 0.1 | 0.1 | 0.1 |
| Glycerol | 2 | 2 | 2 |
| Propylene glycol | 3 | 3 | 3 |
| Poloxamer P124 | 0.1 | 0.1 | 0.1 |
| Allantoin | 0.2 | 0.2 | 0.2 |
| Talc | 2.0 | 2.0 | 2.0 |
| Xanthan gum | 0.5 | 0.5 | 0.5 |
| Lactic acid (qs pH 3.5-4) | Qs pH | Qs pH | Qs pH |
| Dimethicone | 1.0 | 1.0 | 1.0 |
| Cyclomethicone 5 | 8.0 | 8.0 | 8.0 |
| Liquid paraffin | 1.0 | 1.0 | 1.0 |
| Purified water | Qs 100 | Qs 100 | Qs 100 |

EXAMPLE 9

Examples of Compositions of Formulations of Cream Type According to the Invention Prepared from the Primary Emulsions A1 and B1 of Example 3 Containing Trifarotene In order to prepare compositions of cream type according to the invention $I'_C$ to $II'_C$, an amount of primary emulsion prepared according to example 3 was taken and integrated at a predetermined moment during the process for preparing a cream.

To obtain a cream of 100 grams containing 0.01% of Trifarotene, contained in the presence of approximately 5% of solvent oil in the microcapsules, 17.784 grams of the primary emulsion of composition A1 or B1 of example 3 are added to the formulation.

Examples of compositions of cream type obtained according to the invention are thus as follows:

| Ingredients | Compositions (% w/w) | |
| --- | --- | --- |
|  | $I_C'$ | $II_C'$ |
| Trifarotene | 0.01 | 0.01 |
| Diisopropyl adipate | 4.96 | — |
| PPG-15 stearyl ether | — | 4.96 |
| Hydrogenated lecithin | 0.72 | 0.72 |
| Methyl paraben | 0.2 | 0.2 |
| Propyl paraben | 0.1 | 0.1 |
| Sodium acryloyldimethyltaurate copolymer/isohexadecane/polysorbate 80 | 2 | 2 |
| Sodium docusate | 0.05 | 0.05 |
| Disodium edetate | 0.1 | 0.1 |
| Glycerol | 2 | 2 |
| Propylene glycol | 3 | 3 |
| Poloxamer P124 | 0.1 | 0.1 |
| Allantoin | 0.2 | 0.2 |
| Talc | 2.0 | 2.0 |
| Xanthan gum | 0.5 | 0.5 |
| Lactic acid (qs pH 3.5-4) | Qs PH | Qs pH |

-continued

| Ingredients | Compositions (% w/w) | |
|---|---|---|
| | $I_C{}'$ | $II_C{}'$ |
| Dimethicone | 1.0 | 1.0 |
| Cyclomethicone 5 | 8.0 | 8.0 |
| Liquid paraffin | 1.0 | 1.0 |
| Purified water | Qs 100 | Qs 100 |

EXAMPLE 10

Characterization of Composition $I_G$ of Example 7 of Gel Type According to the Invention, Prepared from Primary Emulsions Containing Trifarotene, Obtained According to the Three Processes In the present example, the hydrogenated lecithin is 100% dispersed in the fatty phase.
Each test carried out is described below:
The macroscopic observation is performed on the formulation in its original packaging.
The microscopic observation is performed using an Axio-.Scope A1 microscope (polarized light, objective ×20).
The pH measurement is taken in the formulation.
The viscosity measurement is performed using an apparatus of Brookfield RVDVII+ type. The measurements are performed after 1 min, in the original packaging.

| Equipment | Characterizations | Results |
|---|---|---|
| Polytron | Macroscopic observation | White gel |
| | Microscopic observation | Capsules of micrometric size |
| | pH | 5.14 |
| | Viscosity RV, S06, 10 rpm | 57 200 cP |
| Magic Lab | Macroscopic observation | White gel |
| | Microscopic observation | Capsules of micrometric size |
| | pH | 5.30 |
| | Viscosity RV, S06, 10 rpm | 65 800 cP |
| Sonication | Macroscopic observation | White gel |
| | Microscopic observation | Capsules of micrometric size |
| | pH | 5.19 |
| | Viscosity RV, S06, 10 rpm | 64 600 cP |

Whatever the equipment used, Polytron, Magic Lab or sonication probe, the gels have the same characteristics.

EXAMPLE 11

Study of Stability of the Gels of Example 10 According to the Process Used

Each test carried out is described below:
The macroscopic observation is performed on the formulation in its original packaging.
The microscopic observation is performed using an Axio-.Scope A1 microscope (polarized light, objective ×20).
The pH measurement is taken in the formulation.
The viscosity measurement is performed using an apparatus of Brookfield RVDVII+ type. The measurements are performed after 1 min, in the original packaging.

The Trifarotene titer is verified by HPLC after preparation, the results at T0 are expressed as % of the theoretical real concentration, and the results at T3M are expressed as % of the concentration at T0.

Composition $I_G$ of Example 7 (Diisopropyl Adipate Process by Polytron

| Characterizations | Storage conditions | Stability at 3 months |
|---|---|---|
| Macroscopic appearance | T0 | White gel |
| | AT | IDEM T0 |
| | 4° C. | IDEM T0 |
| | 40° C. | IDEM T0 |
| Microscopic appearance | T0 | Micrometric capsules |
| | AT | IDEM T0 |
| | 4° C. | IDEM T0 |
| | 40° C. | IDEM T0 |
| pH | T0 | pH = 5.14 |
| Viscosity RV, S06, 10 rpm | | 57 200 cP |
| | AT | pH = 4.97 |
| | | 58 100 cP |
| | 40° C. | pH = 4.91 |
| | | 53 800 cP |
| Conclusions | | Stable gel |

Composition $I_G$ of Example 7 (Diisopropyl Adipate Process by Magic Lab

| Characterizations | Storage conditions | Stability at 3 months |
|---|---|---|
| Macroscopic appearance | T0 | White gel |
| | AT | IDEM T0 |
| | 4° C. | IDEM T0 |
| | 40° C. | IDEM T0 |
| Microscopic appearance | T0 | Micrometric capsules |
| | AT | IDEM T0 |
| | 4° C. | IDEM T0 |
| | 40° C. | IDEM T0 |
| pH | T0 | pH = 5.30 |
| Viscosity RV, S06, 10 rpm | | 65 800 cP |
| | AT | pH = 5.22 |
| | | 65 800 cP |
| | 40° C. | pH = NR |
| | | 61 300 cP |
| Trifarotene dosage Rec %/T0 | AT | 101.7% |
| | 40° C. | 103.6% |
| Conclusions | | Stable gel |

Composition $I_G$ of Example 7 (Diisopropyl Adipate Process by Sonication

| Characterizations | Storage conditions | Stability at 3 months |
|---|---|---|
| Macroscopic appearance | T0 | White gel |
| | AT | IDEM T0 |
| | 4° C. | IDEM T0 |
| | 40° C. | IDEM T0 |
| Microscopic appearance | T0 | Micrometric capsules |
| | AT | IDEM T0 |
| | 4° C. | IDEM T0 |
| | 40° C. | IDEM T0 |
| pH | T0 | pH = 5.19 |
| Viscosity | | 64 600 cP |

-continued

| Characterizations | Storage conditions | Stability at 3 months |
|---|---|---|
| RV, S06, 10 rpm | AT | pH = 4.30 |
|  |  | 60 600 cP |
|  | 40° C. | pH = 4.90 |
|  |  | 60 700 cP |
| Trifarotene dosage | AT | 103.6% |
| Rec %/T0 | 40° C. | 104.4% |
| Conclusions |  | Stable gel |

Whatever the type of equipment, the gels containing the microcapsules are stable for 3 months at ambient temperature and at 40° C.

In this respect and in light of the results of examples 4 and 10, the process using the Magic Lab equipment will be preferentially be chosen in the examples to follow.

EXAMPLE 12

Characterization of Compositions $I_G$, $IV_G$ and $V_G$ of Example 6 of Gel Type According to the Invention, Prepared from Placebo Primary Emulsions, Obtained According to Two Different Modes of Introduction of the Hydrogenated Lecithin In the present examples, the equipment that was used for preparing the primary emulsions is the Magic Lab.

| | | Hydrogenated lecithin dispersion mode | |
|---|---|---|---|
| Composition/Oil | Characterizations | 100% aqueous phase Gel No. 1 | 100% fatty phase Gel No. 2 |
| $I_G$/ Diisopropyl adipate | Macroscopic observation | White gel | White gel |
| | Microscopic observation | Capsules of micrometric size | Capsules of micrometric size |
| | pH | 4.37 | 5.41 |
| | Viscosity RV, S06, 10 rpm | 57 800 cP | 56 990 cP |
| $IV_G$/PPG-15 stearyl ether | Macroscopic observation | White gel | White gel |
| | Microscopic observation | Capsules of micrometric size | Capsules of micrometric size but sometimes misshapen |
| | pH | 5.34 | 5.39 |
| | Viscosity RV, S06, 10 rpm | 45 900 cP | 46 500 cP |
| $V_G$/Capric/ caprylic acid triglycerides | Macroscopic observation | White gel | White gel |
| | Microscopic observation | Capsules of micrometric size | Capsules of micrometric size |
| | pH | 5.19 | 5.30 |
| | Viscosity RV, S06, 10 rpm | 52 000 cP | 56 200 cP |

In this table, gel No. 1 corresponds to gels $I_G$, $IV_G$ and $V_G$ of example 6, in which the lecithin was 100% dispersed in the aqueous phase.

In this table, gel No. 2 corresponds to gels $I_G$, $IV_G$ and $V_G$ of example 6, in which the lecithin was 100% dispersed in the oily phase.

Depending on the oil used in the formulation, the hydrogenated lecithin dispersion mode can generate different characteristics.

Figure 2:
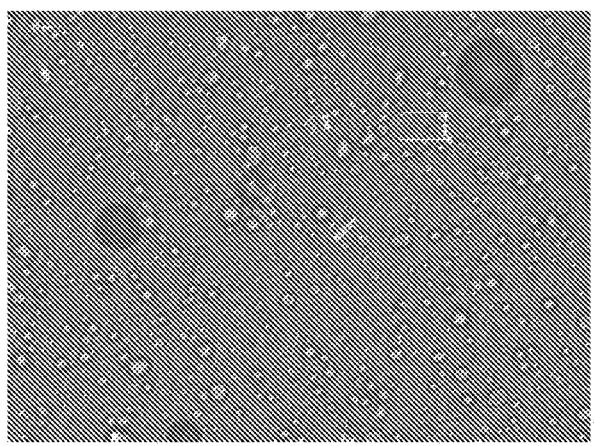
FIG. 2 is a photo image under microscope (objective 40 and magnification x252) of the microcapsules in gel No. 2 prepared from the primary emulsion D containing PPG-15 Stearyl ether as oil, according to the examples.

FIGS. 1 and 2 represent the images obtained under a microscope (objective 40 and magnification ×252) of the microcapsules in gels No. 1 and No. 2 respectively that were prepared from the primary emulsion D containing PPG-15 stearyl ether as oil (gels corresponding to gel $IV_G$ in example 6).

The microscopic observation of the microcapsules reveals that the microcapsules in gels No. 1 and No. 2 differ in terms of polydispersity and shape.

Indeed, it is observed that the microcapsules of FIG. 1 are uniform in size and in shape. On the other hand, those of FIG. 2 are more non-uniform, both in terms of size and in terms of shape. Thus, for a defined oil, the hydrogenated lecithin dispersion mode has an effect on the physical appearance of the microcapsules.

Figure 3:
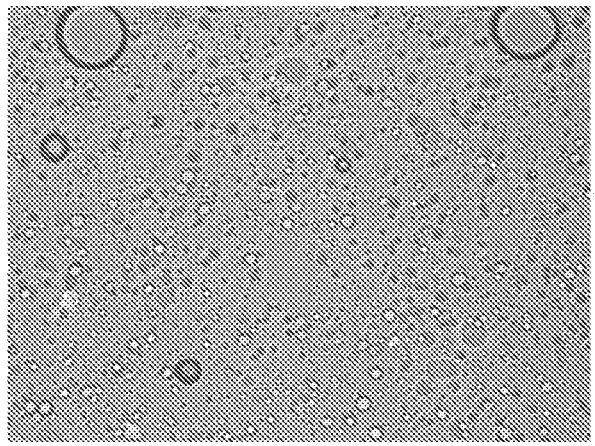
FIG. 3 is a photo image under microscope (objective 40 and magnification x252) of the microcapsules in gel No. 1 prepared from the primary emulsion E containing capric/ caprylic acid triglycerides as oil, according to the examples.
Figure 4:
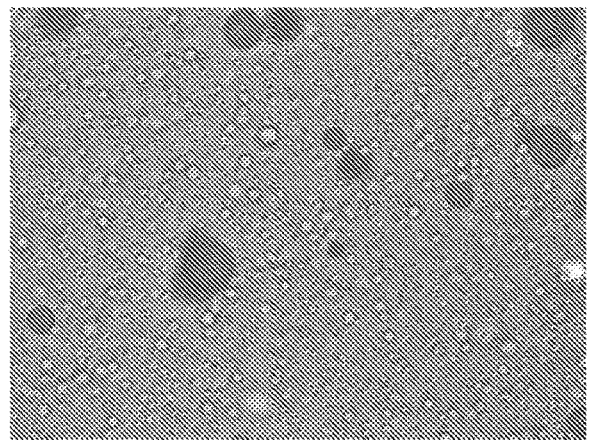
FIG. 4 is a photo image under microscope (objective 40 and magnification x252) of the microcapsules in gel No. 2 prepared from the primary emulsion E containing capric/ caprylic acid triglycerides as oil, according to the examples.

FIGS. 3 and 4 represent the images obtained under a microscope (objective 40 and magnification ×252) of the microcapsules in gels No. 1 and No. 2 respectively that were prepared from the primary emulsion E containing capric/caprylic acid triglycerides as oil (gels corresponding to gel $V_G$ in example 6).

The microscopic observation of the microcapsules reveals that the microcapsules in gels No. 1 and No. 2 do not differ in terms of polydispersity and shape.

Thus, for another defined oil, the hydrogenated lecithin dispersion mode does not have an effect on the physical appearance of the microcapsules.

The observations therefore demonstrate that the conditions which result in a better production of microcapsules can be dependent on the hydrogenated lecithin dispersion mode according to the oil used.

In this respect, a hydrogenated lecithin dispersion mode may be preferred for each oil type.

In one preferred mode according to the invention, with acid esters and triglycerides, for instance diisopropyl adipate, as oily solvent, the preferred hydrogenated lecithin dispersion mode is 100% in the fatty phase.

In one preferred mode according to the invention, with polyethylene glycol ethers, for instance PPG-15 stearyl ether, as oily solvent, the preferred hydrogenated lecithin dispersion mode is 100% in the aqueous phase.

EXAMPLE 13

Study of Stability of Gels No. 1 and No. 2 of Example 12 According to the Oil Used (Compositions $IV_G$ and $V_G$ of Example 6) and According to the Hydrogenated Lecithin Introduction Mode Gel No. 1: Dispersion in Aqueous Phase from Composition $IV_G$ of Example 6 (PPG-15 Stearyl Ether

| Characterizations | Storage conditions | Stability at 6 months |
|---|---|---|
| Macroscopic appearance | T0 | White gel |
|  | AT | IDEM T0 |
|  | 4° C. | IDEM T0 |
|  | 40° C. | IDEM T0 |
| Microscopic appearance | T0 | Micrometric capsules |
|  | AT | Slight deformation of the microcapsules |
|  | 4° C. | Slight deformation of the microcapsules |
|  | 40° C. | Slight deformation of the microcapsules |
| pH | T0 | pH = 5.34 |
| Viscosity |  | 45 900 cP |

-continued

| Characterizations | Storage conditions | Stability at 6 months |
|---|---|---|
| RV, S06, 10 rpm | AT | pH = 5.67 |
| | | 46 100 cP |
| | 40° C. | pH = 6.00 |
| | | 45 900 cP |
| Conclusions | | Stable gel |

Gel No. 2: Dispersion in Fatty Phase from Composition $IV_G$ of Example 6 (PPG-15 Stearyl Ether

| Characterizations | Storage conditions | Stability at 6 months |
|---|---|---|
| Macroscopic appearance | T0 | White gel |
| | AT | IDEM T0 |
| | 4° C. | IDEM T0 |
| | 40° C. | IDEM T0 |
| Microscopic appearance | T0 | Micrometric capsules |
| | AT | Considerable deformation of the microcapsules |
| | 4° C. | Considerable deformation of the microcapsules |
| | 40° C. | Considerable deformation of the microcapsules |
| pH Viscosity | T0 | pH = 5.39 |
| | | 46 500 cP |
| RV, S06, 10 rpm | AT | pH = 5.29 |
| | | 46 300 cP |
| | 40° C. | pH = 5.75 |
| | | 42 800 cP |
| Conclusions | | Gel with deformed microcapsules |

Gel No. 1: Dispersion in Aqueous Phase from Composition $V_G$ of Example 6 (Capric/Caprylic Acid Triglycerides

| | Storage conditions | Stability at 6 months |
|---|---|---|
| Macroscopic appearance | T0 | White gel |
| | AT | IDEM T0 |
| | 4° C. | IDEM T0 |
| | 40° C. | IDEM T0 |
| Microscopic appearance | T0 | Micrometric microcapsules |
| | AT | IDEM T0 |
| | 4° C. | IDEM T0 |
| | 40° C. | IDEM T0 |
| pH Viscosity | T0 | pH = 5.19 |
| | | 52 000 cP |
| RV, S06, 10 rpm | AT | pH = 5.42 |
| | | 50 800 cP |
| | 40° C. | pH = 5.58 |
| | | 49 800 cP |
| Conclusions | | Stable gel |

Gel No. 2: Dispersion in Fatty Phase from Composition $V_G$ of Example 6 (Capric/Caprylic Acid Triglycerides

| | Storage conditions | Stability at 6 months |
|---|---|---|
| Macroscopic appearance | T0 | White gel |
| | AT | IDEM T0 |
| | 4° C. | IDEM T0 |
| | 40° C. | IDEM T0 |
| Microscopic appearance | T0 | Micrometric microcapsules |
| | AT | IDEM T0 |
| | 4° C. | IDEM T0 |
| | 40° C. | IDEM T0 |
| pH Viscosity | T0 | pH = 5.30 |
| | | 56 2000 cP |
| RV, S06, 10 rpm | AT | pH = 5.41 |
| | | 55 800 cP |
| | 40° C. | pH = 5.51 |
| | | 47 600 cP |
| Conclusions | | Stable gel |

Figure 5:
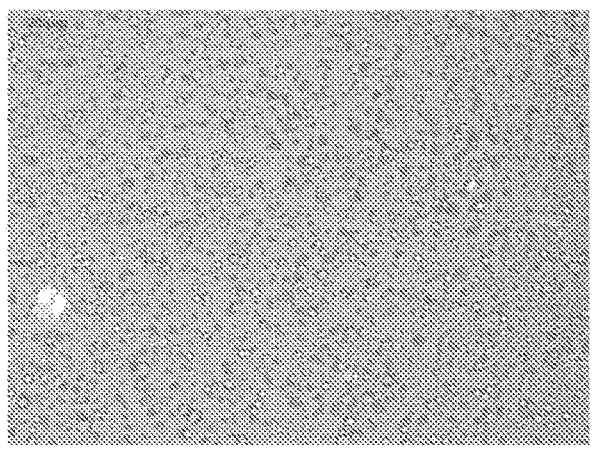
FIG. 5 is a photo image of 100% dispersion of the hydrogenated lecithin in the aqueous phase, according to the examples.
Figure 6:
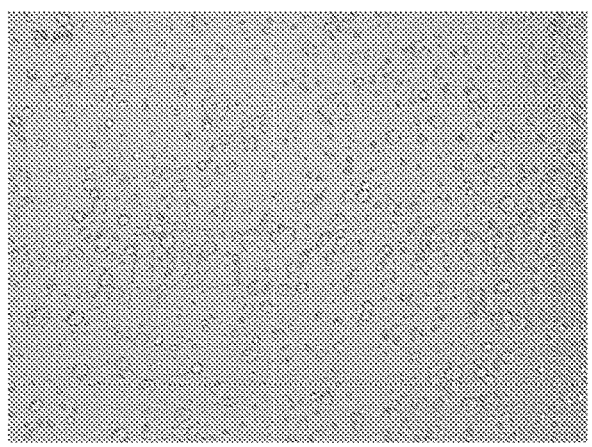
FIG. 6 is a photo image 100% dispersion of the hydrogenated lecithin in the fatty phase, according to the examples.

FIGS. 5 and 6 represent the images obtained under a microscope (objective 40 and magnification ×252) of the microcapsules in gels No. 1 and No. 2 that were prepared from the compositions $IV_G$ containing PPG-15 stearyl ether as oil after 6 months of storage at a temperature of 40° C.

Microscopic observation of the microcapsules in gels No. 1 and No. 2 proves to be significant regarding the stability of the microcapsules according to the hydrogenated lecithin dispersion mode.

With 100% dispersion of the hydrogenated lecithin in the fatty phase, the microcapsules are very non-uniform in size and are deformed (FIG. 6).

With 100% dispersion of the hydrogenated lecithin in the aqueous phase, the microcapsules are more uniform and more even in size (FIG. 5).

The observations therefore demonstrate that the conditions which result in better stability of the capsules over time are 100% dispersion of the hydrogenated lecithin in the aqueous phase, in the case of the use of PPG-15 stearyl ether.

Figure 7:
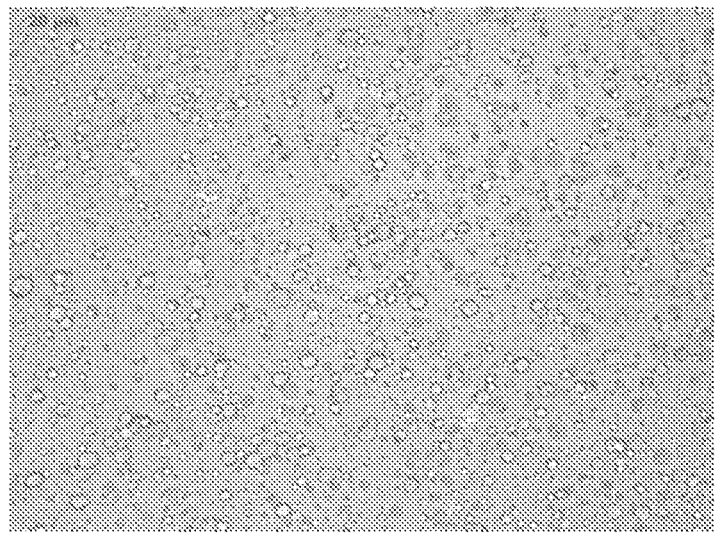
FIG. 7 is a photo image under microscope (objective 40 and magnification x252) of the microcapsules containing capric/ caprylic acid triglycerides triglycerides after 6 months of storage at a temperature of 40° C., according to the examples.
Figure 8:
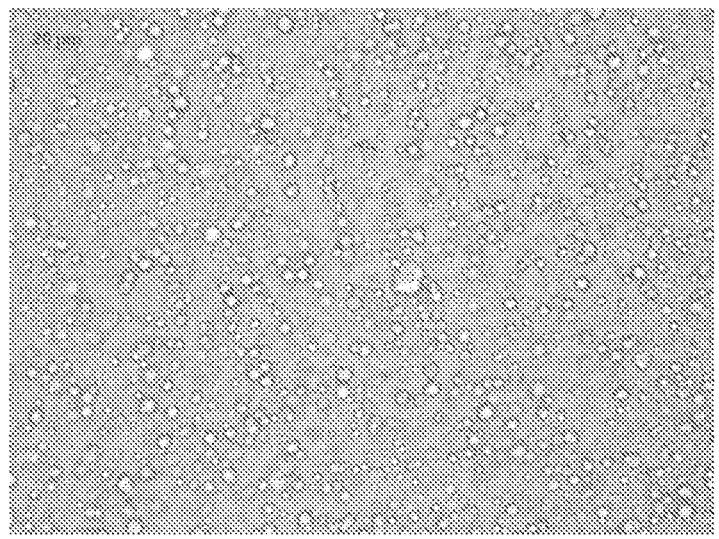
FIG. 8 is a photo image under microscope (objective 40 and magnification x252) of the microcapsules containing capric/ caprylic acid triglycerides triglycerides after 6 months of storage at a temperature of 40° C., according to the examples.

FIGS. 7 and 8 show the images obtained under a microscope (objective 40 and magnification ×252) of the microcapsules containing capric/caprylic acid triglycerides after 6 months of storage at a temperature of 40° C.

The microcapsules are as a whole uniform and even in size, after 6 months of stability at 40° C. (FIGS. 7 and 8).

The observations therefore demonstrate that the conditions which result in stability of the capsules over time can occur with a 100% dispersion of the hydrogenated lecithin in the aqueous phase or a 100% dispersion in the fatty phase, in the case of the use of capric/caprylic acid triglycerides.

In this respect and in the light of the results of examples 12 and 13, a hydrogenated lecithin dispersion mode may be all the more justified for each oil type.

EXAMPLE 14

Characterization of Compositions $I_G'$ and $II_G'$ of Example 7 of Gel Type According to the Invention, Prepared from Primary Emulsions and Containing Trifarotene, Obtained According to the Preferred Hydrogenated Lecithin Introduction Mode According to the Oil Used In the present examples, the equipment that was used for preparing the primary emulsions is the Magic Lab.

The preferred dispersion mode for the hydrogenated lecithin with diisopropyl adipate is 100% in the fatty phase.

The preferred dispersion mode for the hydrogenated lecithin with PPG-15 stearyl ether is 100% in the aqueous phase.

| Composition/ Oil | Characterizations | Results |
|---|---|---|
| $I_G'$/ Diisopropyl adipate | Macroscopic observation | White gel |
| | Microscopic observation | Capsules of micrometric size |
| | pH | 5.11 |
| | Viscosity RV, S06, 10 rpm | 55 600 cP |
| $II_G$/PPG-15 stearyl ether | Macroscopic observation | White gel |
| | Microscopic observation | Capsules of micrometric size |
| | pH | 4.77 |
| | Viscosity RV, S06, 10 rpm | 53 500 cP |

Figure 9:
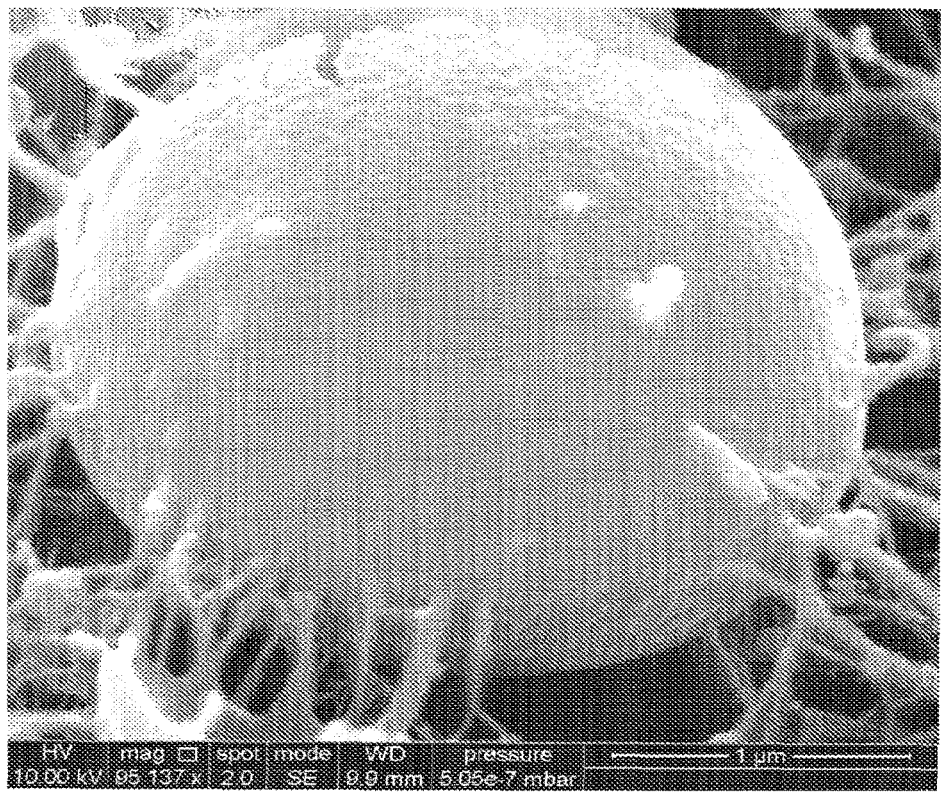
FIG. 9 is a scanning electron microscopy photo of gel No. Id after cyrofracture, according to the examples.

By way of example, Gel No. $I_G'$ is represented in FIG. 9. It was characterized by scanning electron microscopy after cryofracture according to the following protocol:

Freezing in liquid nitrogen and under vacuum

Mechanical fracture

Sublimation (20 minutes at −95° C.)

Metallization (platinum) in order to amplify the secondary electrons

Observation by scanning electron microscopy using an MEB Quanta 250 FEG from FEI

EXAMPLE 15

Study of Stability of the Gels of Example 14 According to the Oil Used and According to the Hydrogenated Lecithin Introduction Mode Dispersion in Fatty Phase Gel Obtained from Composition $I_G'$ of Example 7 (Diisopropyl Adipate

| Characterizations | Storage conditions | Stability at 3 months |
|---|---|---|
| Macroscopic appearance | T0 | White gel |
| | AT | IDEM T0 |
| | 4° C. | IDEM T0 |
| | 40° C. | IDEM T0 |
| Microscopic appearance | T0 | Micrometric capsules |
| | AT | IDEM T0 |
| | 4° C. | IDEM T0 |
| | 40° C. | IDEM T0 |
| pH Viscosity RV, S06, 10 rpm | T0 | pH = 5.11 55 600 cP |
| | AT | pH = 5.15 56 000 cP |
| | 40° C. | 4.97 50 300 cP |
| Conclusions: | | Stable gel |

Dispersion in Aqueous Phase Gel Obtained from Composition $II_G'$ of Example 7 (PPG-15 Stearyl Ether

| Characterizations | Storage conditions | Stability at 3 months |
|---|---|---|
| Macroscopic appearance | T0 | White gel |
| | AT | IDEM T0 |
| | 4° C. | IDEM T0 |
| | 40° C. | IDEM T0 |
| Microscopic appearance | T0 | Micrometric capsules |
| | AT | IDEM T0 |
| | 4° C. | IDEM T0 |
| | 40° C. | IDEM T0 |
| pH | T0 | pH = 4.77 53 500 cP |
| Viscosity RV, S06, 10 rpm | AT | pH = 4.59 50 100 cP |
| | 40° C. | pH = 5.10 48 400 cP |
| Conclusions | | Stable gel |

The results show that gels are obtained which are stable at three months at ambient temperature and at 40° C. in the presence of an active ingredient, namely Trifarotene.

EXAMPLE 16

Characterization of Compositions of Gel Type Prepared from Placebo Primary Emulsions of Composition A of Example 2

In the present examples, the equipment that was used for preparing the primary emulsions is the Magic Lab.

The preferred dispersion mode for the hydrogenated lecithin with diisopropyl adipate is 100% in the fatty phase.

| | | Thickeners | | |
|---|---|---|---|---|
| Primary emulsion/ Oil | Character- izations | sodium acryloyl dimethyltaurate copolymer/ isohexadecane/ polysorbate 80 Composition $I_G$ Gel No. 1 | Carbomer Composition $IX_G$ Gel No. 2 | Crosslinked copolymer Acrylates/ alkyl ($C_{10-30}$) Acrylate Composition $XI_G$ Gel No. 3 |
| 2A/ Diisopropyl adipate | Macroscopic observation | White gel | White gel | White gel |
| | Microscopic observation | Capsules of micrometric size | Capsules of micrometric size | Capsules of micrometric size |
| | pH | 5.12 | 4.87 | 5.03 |
| | Viscosity RV, S06, 10 rpm | 55 400 cP | 64 900 cP | 33 700 cP |

EXAMPLE 17

Study of Stability of the Gels of Example 16

Composition $I_G$ (Diisopropyl Adipate

Gel N°1 (Sodium Acryloyldimethyltaurate Copolymer/Isohexadecane/Polysorbate 80

| Characterizations | Storage conditions | Stability at 3 months |
|---|---|---|
| Macroscopic appearance | T0 | White gel |
| | AT | IDEM T0 |
| | 4° C. | IDEM T0 |
| | 40° C. | IDEM T0 |
| Microscopic appearance | T0 | Micrometric capsules |
| | AT | IDEM T0 |
| | 4° C. | IDEM T0 |
| | 40° C. | IDEM T0 |
| pH Viscosity RV, S06, 10 rpm | T0 | pH = 5.12 55 400 cP |
| | AT | pH = 5.28 51 500 cP |
| | 40° C. | pH = 4.96 47 500 cP |
| Conclusions | | Stable gel |

Composition $IX_G$ (Diisopropyl Adipate), Gel No. 2 (Carbomer

| Characterizations | Storage conditions | Stability at 1 month |
|---|---|---|
| Macroscopic appearance | T0 | White gel |
| | AT | IDEM T0 |
| | 4° C. | IDEM T0 |
| | 40° C. | IDEM T0 |
| Microscopic appearance | T0 | Micrometric capsules |
| | AT | IDEM T0 |
| | 4° C. | IDEM T0 |
| | 40° C. | IDEM T0 |
| pH Viscosity RV, S06, 10 rpm | T0 | pH = 4.87 64 900 cP |
| | AT | pH = 4.86 61 900 cP |
| | 40° C. | pH = 4.86 61 700 cP |
| Conclusions | | Stable gel |

Composition $XI_G$ (Diisopropyl Adipate), Gel No. 3 (Acrylates/C10-30 Alkyl Acrylate Crosspolymer

| Characterizations | Storage conditions | Stability at 1 month |
|---|---|---|
| Macroscopic appearance | T0 | White gel |
| | AT | IDEM T0 |
| | 4° C. | IDEM T0 |
| | 40° C. | IDEM T0 |
| Microscopic appearance | T0 | Micrometric capsules |
| | AT | IDEM T0 |
| | 4° C. | IDEM T0 |
| | 40° C. | IDEM T0 |
| pH Viscosity RV, S06, 10 rpm | T0 | pH = 5.03 33 700 cP |
| | AT | pH = 5.04 34 200 cP |

| Characterizations | Storage conditions | Stability at 1 month |
|---|---|---|
| | 40° C. | pH = 4.99 38 000 cP |
| Conclusions | | Stable gel |

The results show that the gels are stable at one month or three months at ambient temperature or at a temperature of 40° C., whatever the nature of the thickener used.

EXAMPLE 18

Characterization of Compositions $III_G'$ and $IV_G'$ of Example 7 of Gel Type According to the Invention, Prepared from Primary Emulsions and Containing Trifarotene, Obtained According to the Preferred Hydrogenated Lecithin Dispersion Mode According to the Oil Used In the present examples, the equipment that was used for preparing the primary emulsions is the Magic Lab.

The preferred dispersion mode for the hydrogenated lecithin with diisopropyl adipate is 100% dispersion in the fatty phase.

The preferred dispersion mode for the hydrogenated lecithin with PPG-15 stearyl ether is 100% dispersion in the aqueous phase.

| Composition/Oil | Characterizations | Results |
|---|---|---|
| $III_G'$/Diisopropyl adipate | Macroscopic observation | White gel |
| | Microscopic observation | Capsules of micrometric size |
| | pH | 4.23 |
| | Viscosity RV, S06, 10 rpm | 68 300 cP |
| $IV_G'$/PPG-15 stearyl ether | Macroscopic observation | White gel |
| | Microscopic observation | Capsules of micrometric size |
| | pH | 4.16 |
| | Viscosity RV, S06, 10 rpm | 66 600 cP |

EXAMPLE 19

Study of Stability of the Gels of Example 18

Composition $III_G'$(Oil: Diisopropyl Adipate

| Characterizations | Storage conditions | Stability at 3 months |
|---|---|---|
| Macroscopic appearance | T0 | White gel |
| | AT | IDEM T0 |
| | 4° C. | IDEM T0 |
| | 40° C. | IDEM T0 |
| Microscopic appearance | T0 | Micrometric capsules |
| | AT | IDEM T0 |
| | 4° C. | IDEM T0 |
| | 40° C. | IDEM T0 |
| pH Viscosity RV, S06, 10 rpm | T0 | pH = 4.23 68300 cP |
| | AT | pH = 4.09 60 300 cP |

-continued

| Characterizations | Storage conditions | Stability at 3 months |
|---|---|---|
|  | 40° C. | pH = 4.21 |
|  |  | 59 100 cP |
| Trifarotene dosage | AT | 100% |
| Rec %/T0 | 40° C. | 100% |
| Conclusions |  | Stable gel |

Composition IV$_G$'(Oil: PPG-15 Stearyl Ether

| Characterizations | Storage conditions | Stability at 3 months |
|---|---|---|
| Macroscopic appearance | T0 | White gel |
|  | AT | IDEM T0 |
|  | 4° C. | IDEM T0 |
|  | 40° C. | IDEM T0 |
| Microscopic appearance | T0 | Micrometric capsules |
|  | AT | IDEM T0 |
|  | 4° C. | IDEM T0 |
|  | 40° C. | IDEM T0 |
| pH | T0 | pH = 4.16 |
| Viscosity |  | 66 600 cP |
| RV, S06, 10 rpm | AT | 4.12 |
|  |  | 62 400 cP |
|  | 40° C. | 4.30 |
|  |  | 50 300 cP |
| Trifarotene dosage | AT | 100 |
| Rec %/T0 | 40° C. | 100 |
| Conclusions |  | Stable gel |

The results show that the gels containing an active ingredient, namely Trifarotene, are stable at three months at ambient temperature or at a temperature of 40° C. for various gel formulations.

EXAMPLE 20

Characterization of Compositions II$_G$ and III$_G$ of Example 6 of Gel Type According to the Invention, Prepared from Placebo Primary Emulsions of Compositions B and C of Example 2

In the present examples, the equipment that was used for preparing the primary emulsions is the Magic Lab.

The preferred dispersion mode for the hydrogenated lecithin with the diisopropyl adipate is 100% dispersion in the oily phase.

In the table, gel No. 1 corresponds to gel II$_G$ in which the diisopropyl adipate was dispersed in the fatty phase and to gel III$_G$ in which the diisopropyl adipate was dispersed in the fatty phase.

| Oil | Characterizations | Composition II$_G$ Gel No. 1 | Composition III$_G$ Gel No. 2 |
|---|---|---|---|
| Diisopropyl adipate | Macroscopic observation | White gel | White gel |
|  | Microscopic observation | Capsules of micrometric size | Capsules of micrometric size |
|  | pH | 5.24 | 5.15 |
|  | Viscosity | 47 300 Cp (RV, S06, 10 rpm) | 142 000 cP (RV, S07, 10 rpm) |

EXAMPLE 21

Study of Stability of the Gels of Example 20

Composition II$_G$

Gel No. 1 (10% Diisopropyl Adipate

| Characterizations | Storage conditions | Stability at 1 month |
|---|---|---|
| Macroscopic appearance | T0 | White gel |
|  | AT | IDEM T0 |
|  | 4° C. | IDEM T0 |
|  | 40° C. | IDEM T0 |
| Microscopic appearance | T0 | Micrometric capsules |
|  | AT | IDEM T0 |
|  | 4° C. | IDEM T0 |
|  | 40° C. | IDEM T0 |
| pH | T0 | pH = 5.24 |
| Viscosity |  | 47 300 cP |
| RV, S06, 10 rpm | AT | pH = 5.21 |
|  |  | 45 700 cP |
|  | 40° C. | pH = 5.16 |
|  |  | 43 600 cP |
| Conclusions |  | Stable gel |

Composition III$_G$

Gel No. 2 (20% Diisopropyl Adipate

| Characterizations | Storage conditions | Stability at 1 month |
|---|---|---|
| Macroscopic appearance | T0 | White gel |
|  | AT | IDEM T0 |
|  | 4° C. | IDEM T0 |
|  | 40° C. | IDEM T0 |
| Microscopic appearance | T0 | Micrometric capsules |
|  | AT | IDEM T0 |
|  | 4° C. | IDEM T0 |
|  | 40° C. | IDEM T0 |
| pH | T0 | pH = 5.15 |
| Viscosity |  | 142 000 cP |
| RV, S07, 10 rpm | AT | pH = 4.83 |
|  |  | 118 000 cP |
|  | 40° C. | pH = 5.13 |
|  |  | 102 000 cP |
| Conclusions |  | Stable gel |

The results show that the gels obtained are stable at one month at ambient temperature or a temperature of 40° C., whatever the diisopropyl adipate content.

EXAMPLE 22

Characterization of Compositions I$_C$ and III$_C$ of Example 9 of Cream Type According to the Invention, Prepared from Primary Emulsions and Containing Trifarotene, Obtained According to the Preferred Hydrogenated Phosphatidylcholine Introduction Mode According to the Oil Used In the present examples, the equipment that was used for preparing the primary emulsions is the Magic Lab.

The preferred dispersion mode for the hydrogenated lecithin with diisopropyl adipate is 100% dispersion in the fatty phase.

The preferred dispersion mode for the hydrogenated lecithin with PPG-15 stearyl ether is 100% dispersion in the aqueous phase.

| Composition/Oil | Characterizations | Results |
|---|---|---|
| Ic/diisopropyl adipate | Macroscopic observation | White cream |
| | Microscopic observation | Capsules of micrometric size |
| | pH | 4.84 |
| | Viscosity RV, S06, 10 rpm | 72 000 cP |
| IIc/PPG-15 stearyl ether | Macroscopic observation | White cream |
| | Microscopic observation | Capsules of micrometric size |
| | pH | 4.72 |
| | Viscosity RV, S06, 10 rpm | 79 700 cP |

EXAMPLE 23

Study of Stability of the Creams of Example 20

Composition $I_c$ (Diisopropyl Adipate

| Characterizations | Storage conditions | Stability at 1 month |
|---|---|---|
| Macroscopic appearance | T0 | White cream |
| | AT | IDEM T0 |
| | 4° C. | IDEM T0 |
| | 40° C. | IDEM T0 |
| Microscopic appearance | T0 | Micrometric capsules |
| | AT | IDEM T0 |
| | 4° C. | IDEM T0 |
| | 40° C. | IDEM T0 |
| pH Viscosity RV, S06, 10 rpm | T0 | pH = 4.72 79 700 cP |
| | AT | pH = 4.81 82 500 cP |
| | 40° C. | pH = 4.77 67 500 cP |
| Trifarotene dosage Rec %/T0 | AT | 97.9% |
| | 40° C. | 97.0% |
| Conclusions | | Stable cream |

Composition IIc (PPG-15 Stearyl Ether

| Characterizations | Storage conditions | Stability at 1 month |
|---|---|---|
| Macroscopic appearance | T0 | White cream |
| | AT | IDEM T0 |
| | 4° C. | IDEM T0 |
| | 40° C. | IDEM T0 |
| Microscopic appearance | T0 | Micrometric capsules |
| | AT | IDEM T0 |
| | 4° C. | IDEM T0 |
| | 40° C. | IDEM T0 |
| pH Viscosity RV, S06, 10 rpm | T0 | pH = 4.84 72 000 cP |
| | AT | pH = 5.05 71 700 cP |
| | 40° C. | pH = 5.04 64 500 cP |
| Trifarotene dosage Rec %/T0 | AT | 98.8% |
| | 40° C. | 97.3% |
| Conclusions | | Stable cream |

EXAMPLE 24

Study of In Vitro Skin Penetration of Trifarotene Encapsulated in Microcapsules According to Example 14, Dispersed in a Gel Conditions of the Study:

In this study, the formulations were applied for 16 hours to the surface of the skin. At the end of the application, the Trifarotene is quantified in the various skin compartments: stratum corneum, epidermis, dermis and receiving liquid according to a validated bioanalysis method performed by positive electrospray ionization tandem mass spectrometry, using a Xevo machine (Waters). The quantification limit for Trifarotene is 1 ng/ml. The LC/MS/MS conditions developed made it possible to detect up to 0.1% of the dose applied in each of the compartments (dose not absorbed, stratum, epidermis, dermis and receiving liquid).

The details of the cutaneous application are given in the table below:

| Skin: 3 donors, 3 samples per donor | |
|---|---|
| Source | Whole abdominal human skin |
| Franz cells | 2 cm$^2$ |
| Receiving liquid volume | 3 ml |
| Barrier function | Evaluated by determination of insensible water loss, acceptable unless contraindication |
| Reference gel containing 100 µg/g Trifarotene | |
| Gel No. II$_{G'}$ example 14 (Dispersion 100% Fatty phase) containing 100 µg/g Trifarotene | |
| Gel No. I$_{G'}$ example 14 (Dispersion 100% Aqueous phase) containing 100 µg/g Trifarotene | |

| | Application |
|---|---|
| Application | ~2 mg/cm$^2$ |
| Amount of active agent applied | 142~241 ng/cm$^2$ |
| Number of cells per formulation | 6 |
| Number of donors per formulation | 3 |
| Exposure time | 16 h |

| Sample assay | |
|---|---|
| Washing of donor compartment and wiping | "Excess"/Dose not absorbed |
| 1st strip | |
| Stratum corneum (2-15 strips max) | Total Skin |
| Epidermis | |
| Dermis | |
| Receiving Liquid | Dose absorbed |
| LC/UV and LC/MS analyses | |
| Quantification limit | 1 ng/ml |

The two formulations tested have the same composition as composition $I_G'$ of example 7 and were produced with the Magic Lab.

Only the hydrogenated phosphatidyl choline introduction mode differentiates the two gels.

The formula of the reference gel is as follows:

| Ingredients/INCI names | Composition (% w/w) |
|---|---|
| Trifarotene | 0.01 |
| Propylene Glycol | 30.00 |
| Ethanol 95-96% | 67.99 |
| Hydroxypropylcellulose | 2.00 |

Figure 10:
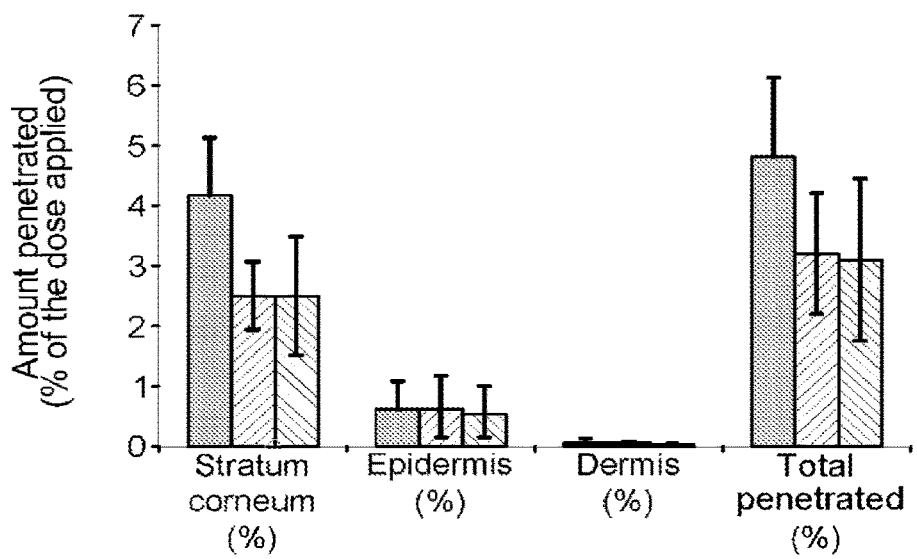
FIG. 10 is a bar graph illustrating the amount of Trifarotene penetration as a percentage of the dose applied according to the various skin compartments, according to the examples.

Results:

The results presented in FIG. 10 show the amount penetrated as a percentage of the dose applied (% dose applied) according to the various skin compartments.

Conclusions:

The total penetration of Trifarotene from the various gels containing encapsulated Trifarotene is less than the reference in which the Trifarotene is dissolved but not encapsulated.

For the reference comprising Trifarotene, the amount penetrated is about 4.86%.

For the gels containing the microcapsules, the amount penetrated ranges from 3.17% to 3.25%.

The total penetration of the encapsulated Trifarotene is similar whatever the phosphatidylcholine dispersion mode:

With 100% dispersion in the oily phase, the total amount penetrated is: 3.25±1.00%.

With 100% dispersion in the aqueous phase, the total amount penetrated is: 3.17±1.38%.

The epidermal and dermal tissue distribution of Trifarotene is similar whether or not it is encapsulated.

With the microcapsules, the tissue distribution of Trifarotene is similar whatever the hydrogenated phosphatidylcholine dispersion mode.

Thus, the encapsulation of Trifarotene decreases the amount penetrated at the level of the stratum corneum without however modifying the tissue distribution of said Trifarotene.

The invention claimed is:

1. A lipid microcapsule comprising an oily internal phase and a non-polymeric shell obtained from at least one lipid compound, wherein: the at least one lipid compound is a hydrogenated lecithin; the oily internal phase consists of a fatty substance and Trifarotene dissolved in the fatty substance; a weight ratio of the internal oily phase and the hydrogenated lecithin is from 5:1 to 7:1; the microcapsule is free of organic solvent of alcoholic type; and the microcapsule has a mean size of from 1 µm to 80 µm and the Trifarotene is stable for three months at ambient temperature and 40° C.

2. The microcapsule as claimed in claim 1, wherein the at hydrogenated lecithin has greater than 85 wt % phosphatidylcholine.

3. The microcapsule as claimed in claim 1, wherein the at least one lipid compound is present in an amount of from 0.01% to 10% by weight relative to the total weight of the microcapsule.

4. The microcapsule as claimed in claim 1, wherein the at least one lipid compound has a transition temperature greater than 35° C.

5. The microcapsule as claimed in claim 1, wherein the Trifarotene is present in an amount of from 0.00001% to 1% by weight relative to the total weight of the composition.

6. The microcapsule as claimed in claim 1, wherein the microcapsule is free of co-surfactant.

7. The microcapsule as claimed in claim 1, wherein the microcapsule is free of volatile organic solvent.

8. The microcapsule as claimed in claim 1, wherein the microcapsule is free of polymer.

9. The microcapsule as claimed in claim 1, wherein the fatty substance is liquid or semiliquid at ambient temperature.

10. The microcapsule as claimed in claim 1, wherein the fatty substance is selected from the group consisting of polyethoxylated fatty acids, triglycerides and oils comprising same, fatty acid esters and polyethylene glycol ethers.

11. The microcapsule as claimed in claim 10, wherein the fatty substance is a fatty add ester or polyethylene glycolether.

12. The microcapsule as claimed in claim 1, wherein the fatty substance is diisopropyl adipate or PPG-15 stearyl ether.

13. The microcapsule as claimed in claim 1, wherein the fatty substance is present in an amount of from 50% to 99.997% by weight relative to the total weight of the internal phase.

14. An emulsion of oil-in-water type comprising a plurality of the microcapsules as claimed in claim 1, wherein the microcapsules are dispersed in an aqueous phase.

15. The emulsion as claimed in claim 14 wherein the weight ratio of the water and the internal oily phase is from 1.5:1 to 5:1.

16. A composition comprising in a pharmaceutically acceptable carrier, the emulsion as claimed in claim 14.

17. The composition as claimed in claim 16, wherein the pharmaceutically acceptable carrier is a gel.

18. The composition as claimed in claim 16, wherein the pharmaceutically acceptable carrier is a solution.

19. The composition as claimed in claim 16, wherein the pharmaceutically acceptable carrier is a cream.

20. The composition as claimed in claim 16, wherein the microcapsules comprise, based on a weight basis relative to the total weight of the composition:
(a) 0.01% to 10% of the lipid compound;
(b) 0.1% to 50% of the fatty substance; and
(c) 0.00001% to 0.3% of Trifarotene.

21. The composition as claimed in claim 16, wherein the composition comprises, in a pharmaceutically acceptable carrier, on a weight basis relative to the total weight of the composition:
(a) 0.1% to 1% of hydrogenated lecithin;
(b) 1% to 5% of fatty acid esters or of polyethylene glycol ethers; and
(c) 0.001% to 0.03% of Trifarotene.

22. The composition as claimed in claim 16, wherein the composition is for topical administration.

23. The composition as claimed in claim 16, wherein the composition is a medicament.

24. The microcapsules as claimed in claim 1, wherein the at least one mean size of the microcapsules is from 1 µm to 50 µm.

25. The microcapsules as claimed in claim 1, wherein the mean size of the microcapsules is from 1 µm to 20 µm.

26. The microcapsule as claimed in claim 3, wherein the at least one lipid compound is present in an amount of from 0.05% to 5% by weight relative to the total weight of the microcapsule.

27. The microcapsule as claimed in claim 3, wherein the at least one lipid compound is present in an amount of from 0.1% to 1% by weight relative to the total weight of the microcapsule.

28. The microcapsule as claimed in claim 4, wherein the transition temperature of the at least one lipid compound is greater than 45° C.

29. The microcapsule as claimed in claim 5, wherein the Trifarotene is present in an amount of from 0.001% to 0.05% by weight relative to the total weight of the composition.

30. The microcapsule as claimed in claim 5, wherein the Trifarotene is present in an amount of from 0.003% to 0.03% by weight relative to the total weight of the composition.

31. A method of treating a dermatological complaint selected from the group consisting of acne, ichthyosis, ichthyosiform conditions, palmoplantar hyperkeratosis and psoriasis, the method comprising administering an effective amount of the composition as claimed in claim 16 to an individual subject in need thereof.

32. The method as claimed in claim 31, wherein the dermatological complaint is acne.

* * * * *